United States Patent [19]

Kennedy et al.

[11] Patent Number: 4,848,159

[45] Date of Patent: Jul. 18, 1989

[54] ULTRASONIC INSPECTION PROBE FOR LAMINATED STRUCTURES

[75] Inventors: James C. Kennedy, Bellevue; William M. Lankelis, North Bend; Edward L. Puckett, Snoqualmie; Fred D. Young, Bellevue, all of Wash.

[73] Assignee: The Boeing Company, Seattle, Wash.

[21] Appl. No.: 53,346

[22] Filed: May 22, 1987

[51] Int. Cl.$^4$ .......................................... G01N 29/04
[52] U.S. Cl. ...................................... 73/641; 73/588; 73/598; 73/600
[58] Field of Search ................. 73/628, 632, 633, 640, 73/641, 588, 636, 598, 600

[56] References Cited

U.S. PATENT DOCUMENTS 3,809,607  5/1974  Murray et al. ........................ 73/633
3,813,926  6/1974  Stubbeman ........................... 73/627

OTHER PUBLICATIONS

Hagemaier, D. J. et al., "Ultrasonic Inspection of Carbon-Epoxy Composites", Materials Evaluation, vol. 43, Apr. 1985, 73/588.
Brase, J. et al., "An Automated Ultrasonic Test Bed", Materials Evaluation, 42, Dec. 1984.
Krautkrämer, J. et al., "Ultrasonic Testing of Materials", 2nd Ed., (1977), pp. 405, 496–499, 507–512.

Primary Examiner—Stewart J. Levy
Assistant Examiner—Lawrence G. Fess
Attorney, Agent, or Firm—Christensen, O'Connor, Johnson & Kindness

[57] ABSTRACT

An ultrasonic inspection probe for locating and sizing flaws in the radius region (20) and adjacent areas of a laminated structure (10), such as a composite "T" stiffener (30). The probe includes a plurality of shoes (48, 50, 52, 54, 56, 58) that are arranged for coordinated movement relative to the part under inspection. Each shoe includes a plurality of ultrasonic transducers that are arranged in predetermined adjacent relationships to one another and operated in timed sequence in one or more through-transmission, pulse echo or loss-of-back modes to effect an ultrasonic scan in one direction through the part while the transducers are moved together in another direction along the part. Inspection of the radius region is effected using combinations of angular pulse echo inspection (PEF, PEA, LL45P, RL45P), "radius-to-radius" through-transmission inspection at an angle through the radius region (RTT, RTR, L37.5T, L37.5R, U37.5T, U37.5R), and "flange-to-radius" through-transmission inspection normally into the upper flange (RU45T) and angularly out through the radius RU45R, LU45R).

34 Claims, 15 Drawing Sheets

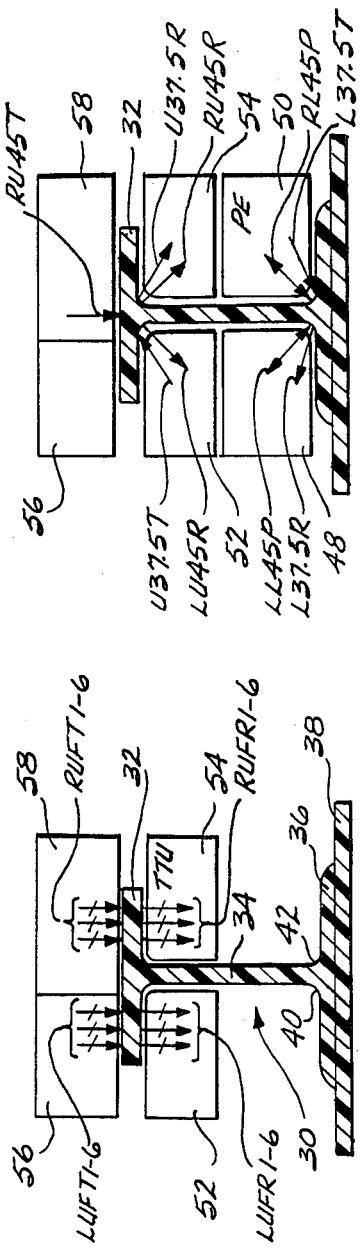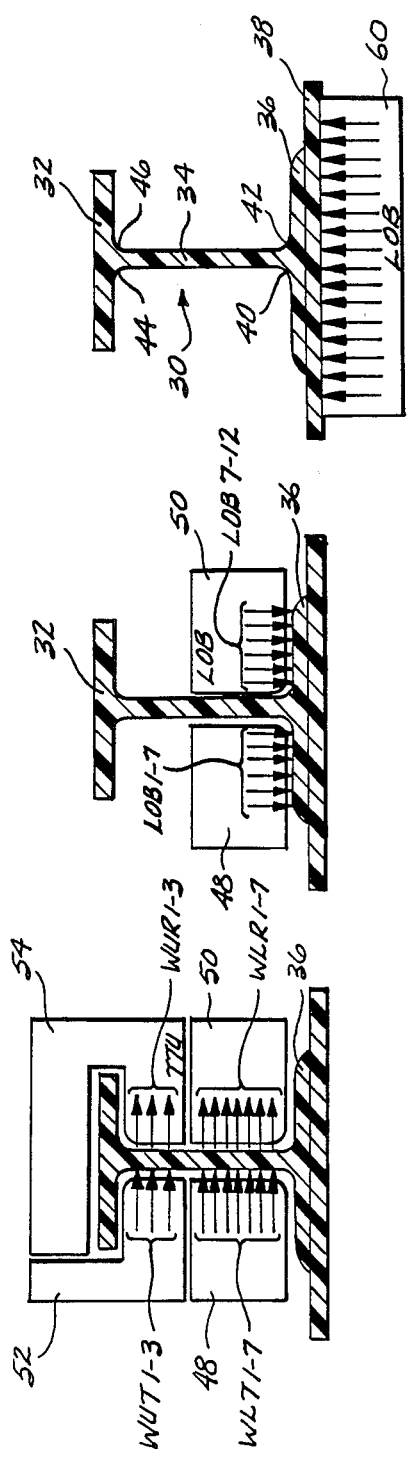

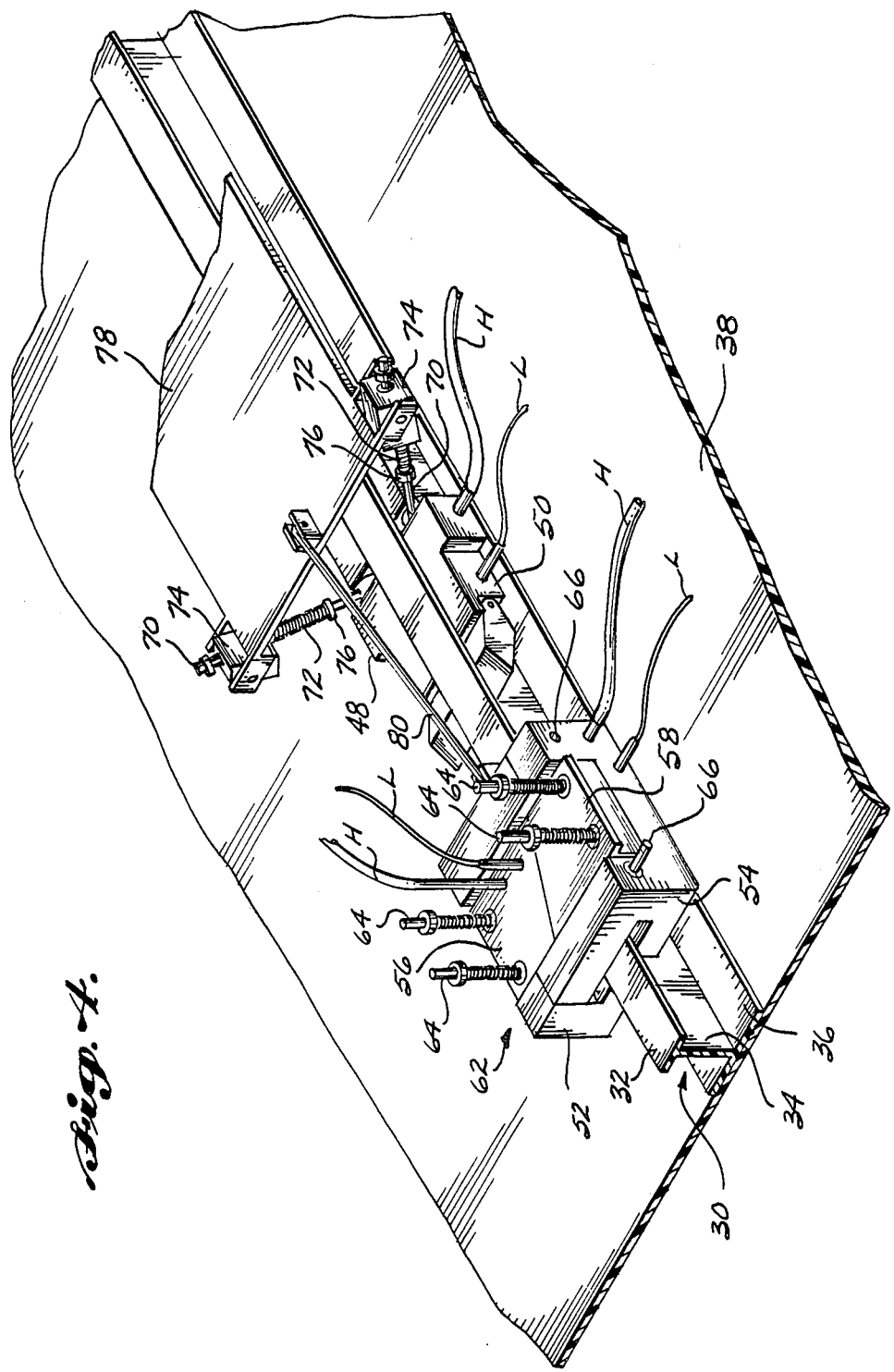

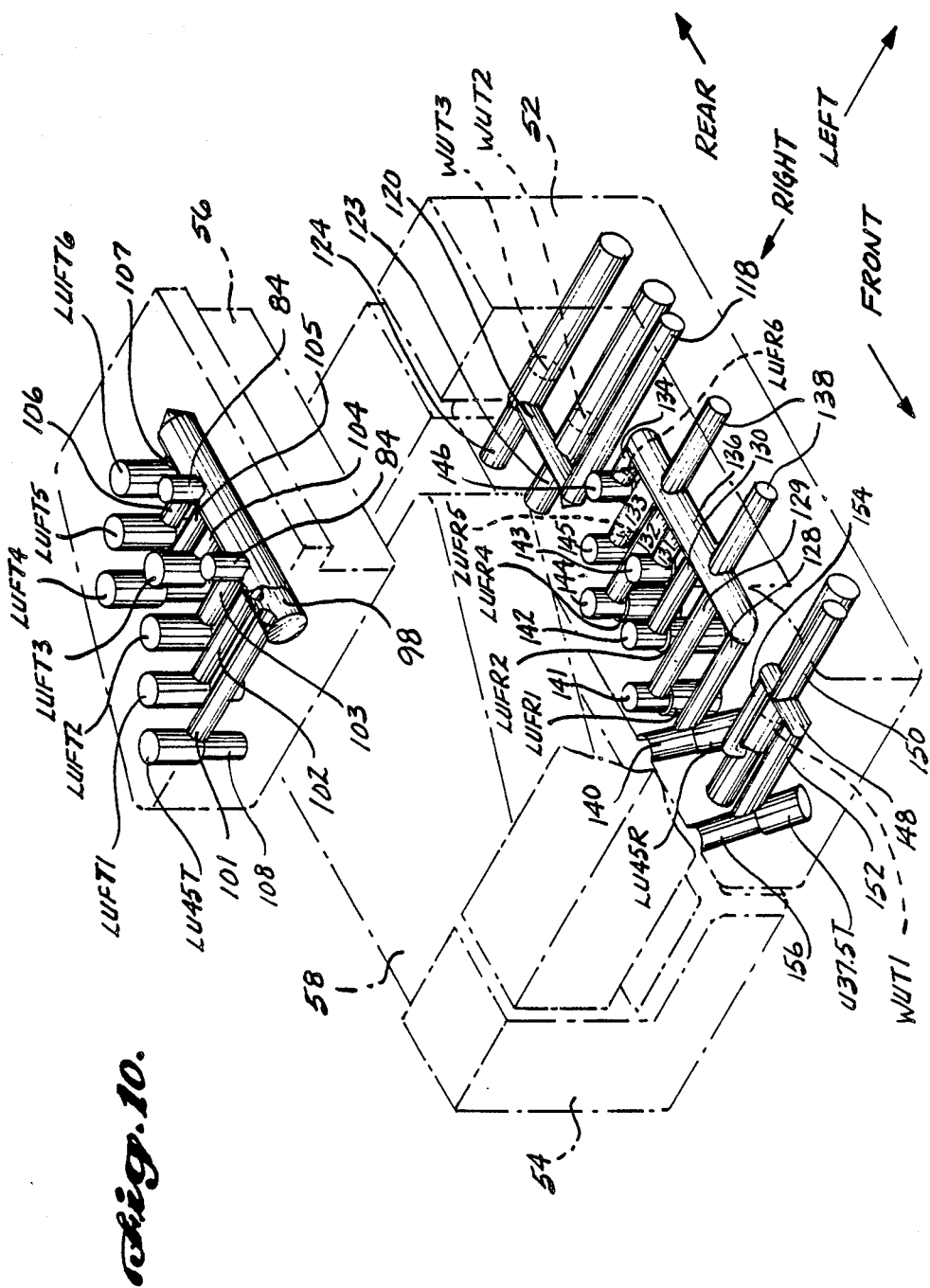

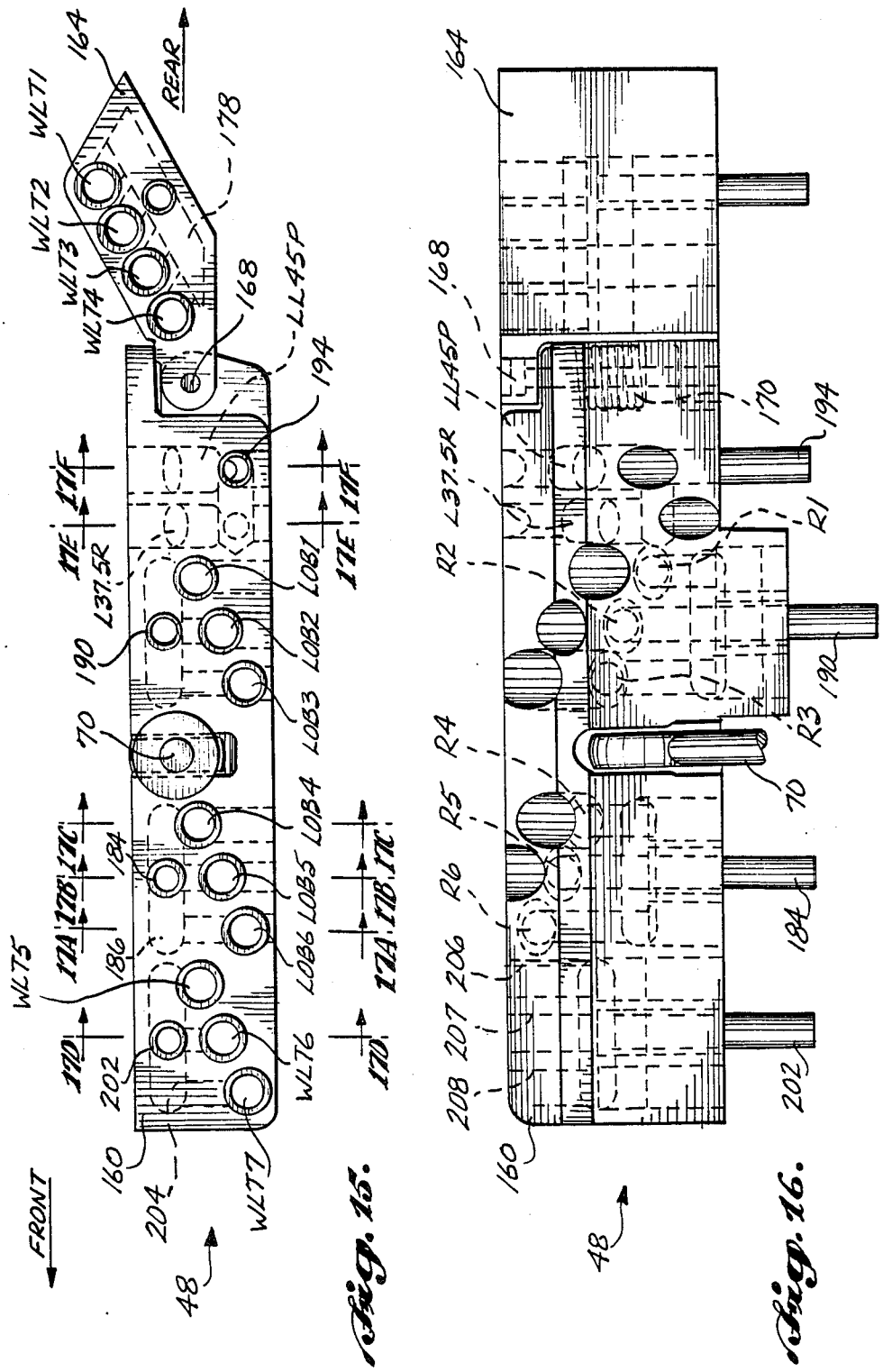

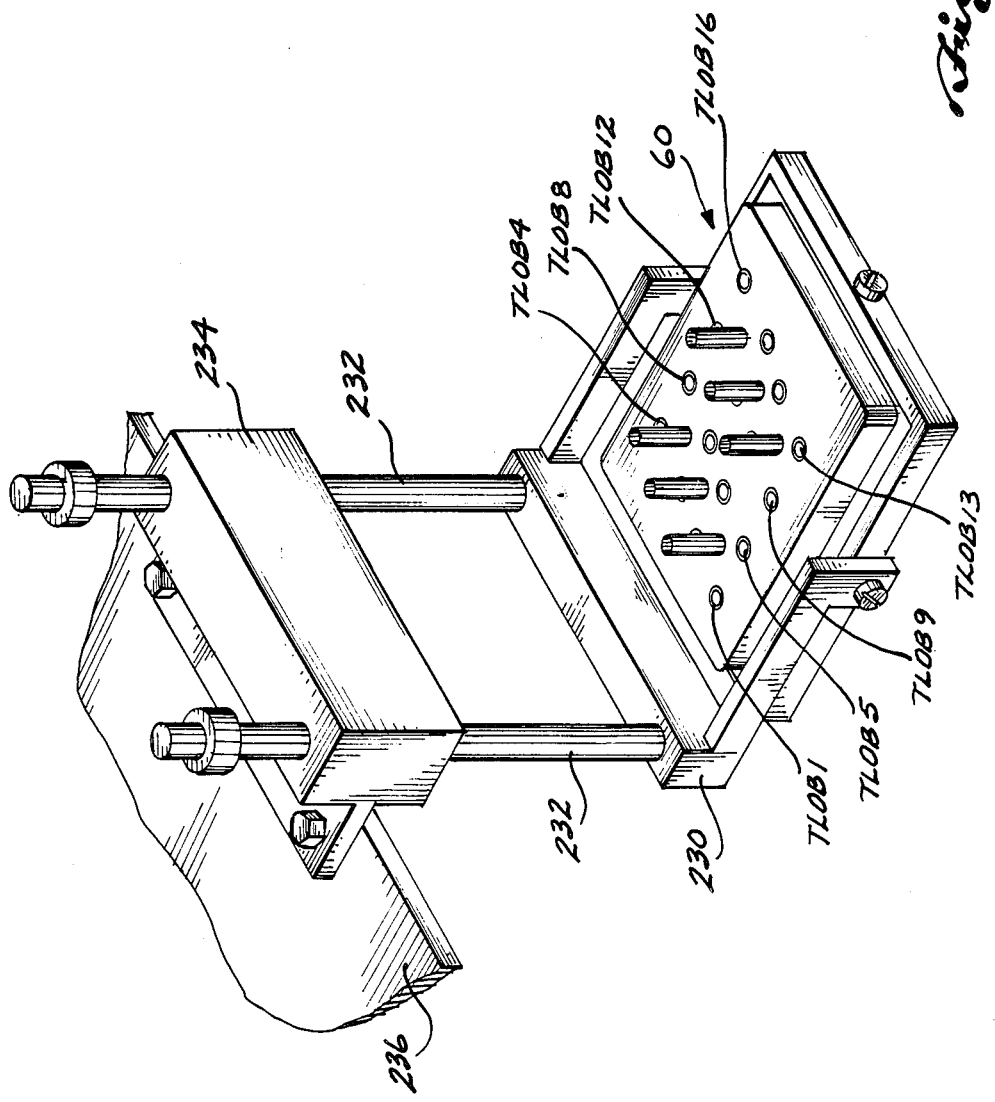

ULTRASONIC INSPECTION PROBE FOR LAMINATED STRUCTURES

BACKGROUND OF THE INVENTION

The present invention relates in general to ultrasonic inspection and, more particularly, to the use of ultrasonic transducers to detect and size flaws in composite or other laminated structures.

The use of composites for aircraft structures has experienced a significant growth in recent years. Such structures are typically formed by curing or consolidating multiple layers of graphite/epoxy or other fibers resin composite materials into a laminate of desired configuration. As fabrication techniques have improved, it has become possible to produce large-scale composite panels having stiffeners integrally molded thereto. These stiffeners have been variously shaped, ranging from simple plate-like blades to angled structures having a T, I, L, or Z cross-sectional configuration.

Heretofore, composite structures have been principally inspected with a hand-scanning method in which a hand-held yoke, carrying either through-transmission or pulse echo transducers, is manipulated by hand over the part under study. While the hand-scan methods have been successfully used to locate flaws in composite structures, they have not been entirely satisfactory. For example, since the technique is dependent upon the freehand guidance of the yoke by the operator, the technique is inherently slow and unreliable since there is no assurance that there will be 100% coverage of the part under inspection. In addition, since the operator must simultaneously manipulate the yoke and observe and analyze a displayed output of the ultrasonic transducers, it is difficult to accurately and reliably identify and locate flaws.

In addition to the foregoing disadvantages, these prior arrangements have failed to adequately and reliably provide information concerning flaws in the critical junction or radius regions where two composite elements intersect as, for example, where a stiffener is integrally joined to a skin panel. In these regions, layers of piles on opposite sides of the stiffener smoothly curve through a bend (typically 90 degrees) and then diverge away from one another where the stiffener meets the skin panel. As a result of this divergence, there exists a cavity of filler area of generally triangular cross-sectional shape having a flat base formed by the skin panel and two concave sides formed by the facing surfaces of the bent portions of the layers that make up the stiffener. In the production process, this filler area is completely filled in a variety of ways to provide a solid structure.

From an inspection standpoint, this filler area is critical since delamination occurring adjacent the bottom or sides of the filler region can result in a loss of up to approximately 80% of the strength of the part. A decrease in strength can also occur as a result of voids in the filler region itself. Despite these significant concerns, it has proved to be a difficult and complex task to locate flaws in the radius region of such composite parts. It is altogether a different and much more difficult task to properly size the flaw so that its impact on the strength of the part may be fully assessed. This difficulty occurs because of the differences in the orientation and actual construction of flaws in composite or other laminated materials relative to the flaws or voids that occur in homogeneous materials.

The flaws in composite or other laminate materials tend to follow the direction of the plies or laminates. In addition, the laminates themselves and their constituent fibers tend to act as waveguides so that there is little predictability concerning the direction that injected sound will follow. These difficulties are even more pronounced in the radius region, owing to the curvature of the laminates and the nature of the filler region, where flaws or voids of many different shapes and orientations are possible. As a consequence, prior inspection techniques that rely upon amplitude sensing are not well suited for inspecting laminated structures and, particularly, the critical radius regions thereof.

The present invention aims to overcome these disadvantages by providing a new and unique ultrasonic inspection apparatus that can be used to make a single-pass, automated inspection of laminated parts. A further and principal aim is to provide such an apparatus that can provide substantially 100% coverage of the part being inspected, including any radius and blade shadow regions.

SUMMARY OF THE INVENTION

The present invention provides an ultrasonic inspection technique and ultrasonic probes that implement that technique, for locating and sizing flaws in the radius region and adjacent areas of a laminated structure. According to the invention technique, a plurality of ultrasonic transducers are arranged in predetermined adjacent relationships to one another and operated in timed sequence in one or more through-transmission, pulse echo, or loss-of-back modes to effect an ultrasonic scan in one direction through a laminated part while the transducers are moved together in another direction along the part. The probe employed to implement this technique includes a pair of shoes that are configured for complementary engagement with opposite sides of the radius region of the part. Each shoe includes a plurality of ultrasonic transducers mounted in fixed position so as to be oriented at predetermined, fixed angles relative to the part when the shoes are engaged therewith. The shoes incorporate internal passages through which water may be caused to flow at an intermediate rate to provide ultrasound coupling between the transducers and parts. To maintain consistent spacing between the transducers and parts, while at the same time enabling the accommodation of varying part thickness or configuration, the shoes are preferably mounted for coordinated translational movement relative to the part under the influence of biasing means, which normally urge the shoes toward engagement with one another.

In accordance with a preferred aspect of the invention, the shoes utilized to inspect the intersection between a blade stiffener and a skin panel or between a skin panel and the web of an "I" or other flanges stiffener include one or more through-transmission transducers for inspecting the portion of the blade or web adjacent the radius area, one or more pulse echo transducers for inspecting the radius area, and one or more transducers operated in a pulse echo loss-of-back mode to inspect the portions of the skin panel adjacent the radius area on either side of the flange or web. In this arrangement, the through-transmission and the loss-of-back transducers are oriented to direct ultrasonic energy substantially normal to the blade, web, or skin portions of the structure, while the pulse echo transducers are oriented to inject sound at an angle into the radius area and the filler region therein.

According to another aspect of the invention, further information concerning flaws in the radius area is obtained by including an additional pair of transducers that are arranged to be operated in a modified through-transmission mode. In this "angular in/angular out" (or "radius-to-radius") through-transmission arrangement, the sending transducer is located on one of the shoes and oriented to inject sound at an angle into the radius area. A portion of that sound travels through the filler area and is received by the other transducer, which is mounted in the other shoe on the opposite side of the radius area and at the same angle as the sending transducer.

The use, just described, of loss-of-back inspection of a skin panel and a combination of angular pulse echo and "angular in/angular out" ("radius-to-radius") through-transmission inspection of the blade-skin or web-skin intersection permits single-sided inspection of a structure, wherein all of the necessary transducers are mounted in shoes that can be manipulated along one side of the structure being inspected. This "single-sided inspection" approach is a practical and economic choice when inspecting parts having sizes or configurations that make it difficult or expensive to provide and synchronously manipulate shoes on both sides of the structure. A large, discretely stiffened composite panel is one example of the structures for which this approach is well suited.

There are a number of laminated structures of interest whose size and configurations are such as to permit "double-sided inspection," i.e., single-pass inspection of a structure with transducers moved in pairs along opposite sides of the structure. Examples of structures suitable for this form of inspection include upstanding blades or webs, and the flanges or caps on the free ends of "I" or "T" stiffeners. Since opposite sides of the flat areas of these structures are readily accessible, it is relatively easy to inspect these areas using shoes that have aligned pairs of transducers operating in a through-transmission inspection mode. However, inspection of the radius and filler areas of these structures remains a difficult task, since the flaws occurring in these regions are as difficult to detect and size as the flaws occurring in the radius and filler regions of the blade-skin intersection discussed above.

In accordance with a further aspect of the invention, inspection of the radius areas and filler regions of those structures is accomplished using another modified form of through-transmission inspection that takes advantage of the accessibility of the free flanges or caps. According to this technique, referred to herein as "angular in/normal out" through-transmission inspection (or "radius-to-flange inspection" or "double-sided radius inspection"), sound is injected at an angle into the radius area by a transmitting transducer. A portion of this sound traverses through the filler area and out through the "top" of the flange or cap where it is picked up by a receive transducer.

A double-sided inspection probe constructed according to this form of the invention to inspect the radius and adjacent area of the flange of an "I" stiffener of similar laminated structure includes a pair of shoes that are configured complementary to the structure and spring-biased toward one another so as to clamp the flange therebetween. The shoes include transmit and receive transducers that are aligned in pairs and operated in a through-transmission mode to inspect the flat areas of the flange. To inspect the radius areas of the flange, each of the shoes that engage the underside of the flange has a transducer that is oriented to inject sound at an angle into the radius area. The portion of this sound that traverses upward through the filler area is picked up by a receive transducer that is located in a shoe that engages the top of the flange. In a preferred form of the invention, the sending transducer is oriented to direct sound at a 45 degree angle into the radius and each received transducer is oriented substantially normal to the top of the flange, aligned with its associated sending transducer, and in line with the edge of the web on the side of the radius being inspected.

While this "angular in/normal out" modified through-transmission technique provides reliable data concerning the flaws in the radius area, it may be desirable to provide for additional inspection of this area because of the complex nature of the flaws that are likely to be encountered in and around the filler region. For this purpose, it is preferable to employ the "radius-to-radius" through-transmission technique that is used to inspect the radius area of the blade-skin intersection. For this purpose, an additional pair of "angular in/angular out" through-transmission transducers are arranged at angles relative to the web and on opposite sides thereof so that sound is injected at an angle into the radius on one side of the web and a portion thereof is received at the same angle but on the opposite side of the web.

Using combinations of the two modified through-transmission techniques (angular in/angular out and angular in/normal out) and the pulse echo technique to inspect the radius area, it is possible to configure a wide variety of ultrasonic inspection probes that will enable substantially 100 percent coverage of a part in a single-pass operation. The number, size, and configuration of the shoes used to form a particular probe and the positioning and orientation of the transducers therein are dictated in part by the shape and configuration of the structure being inspected and in part by the means being used to transport or manipulate the probe during inspection. In accordance with further aspects of the invention, these factors are accommodated by probes ranging from those in which the shoes are spring-biased toward one another, such that the probe is an integral part that effectively holds itself to the structure, to probes consisting of multiple pairs of shoes that are tandemly mounted to a separate probe holder so as to have a number of degrees of freedom of movement. Probes of this latter type are particularly desirable for production purposes since they may be mounted to an overhead gantry robot.

BRIEF DESCRIPTION OF THE DRAWINGS

The invention can best be understood by the following portion of the specification, taken in conjunction with the accompanying drawings in which:

FIGS. 3A through 3E are a series of pictorial rear elevational views showing an arrangement of shoes and the location of ultrasonic transducers therein for inspecting a composite "I" stiffened panel in accordance with the invention;

FIG. 4 is a simplified isometric view of one embodiment of an ultrasonic inspection probe formed in accordance with the invention for inspecting a composite "I" stiffened panel;

FIG. 10 is a simplified isometric view, with parts broken, of the upper flange/web shoe assembly of the probe of FIG. 4, showing the internal water passages;

FIG. 15 is a side elevational view of the left lower flange shoe of the probe of FIG. 4;

FIG. 16 is a plan view of the left lower flange shoe of the probe of FIG. 4;

FIG. 18 is an isometric view of a toolside shoe that may be used in conjunction with the probe of FIG. 4;

DETAILED DESCRIPTION OF THE PREFERRED EMBODIMENT

Figure 1:
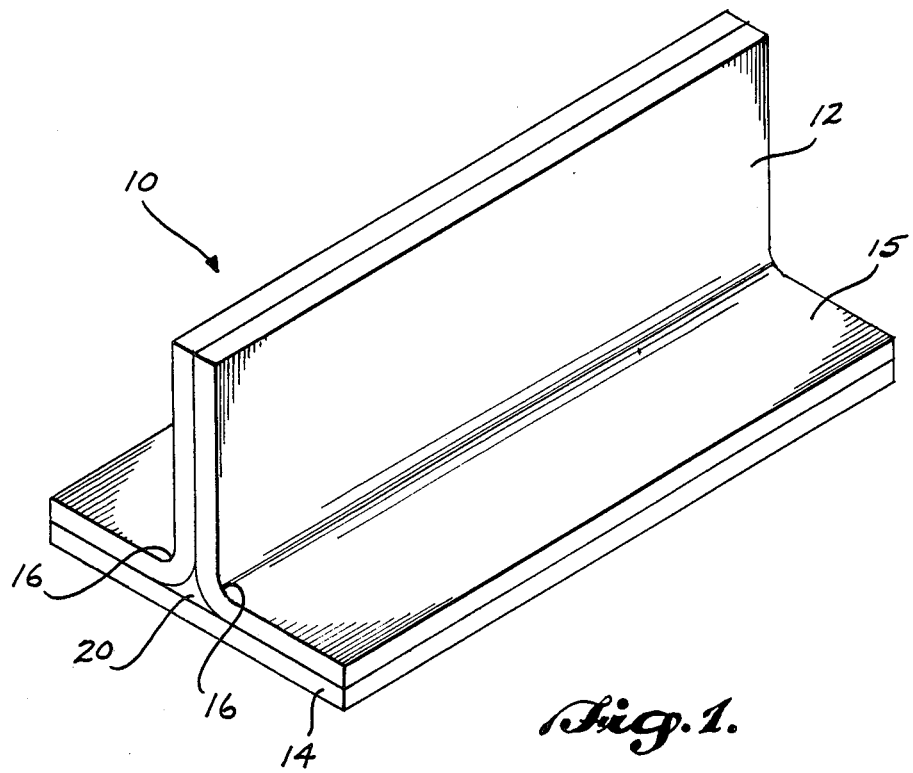
FIG. 1 is a pictorial perspective view of a blade-stiffened laminate structure.

Prior to describing the details of the preferred embodiment of an ultrasonic inspection probe formed in accordance with this invention, the nature of the structure to be inspected will be described to facilitate an understanding of the manner in which the invention solves the problem of inspecting the junction regions that exist between intersecting elements of integrally formed composite or other laminated structures. In this regard, attention is directed to FIGS. 1 and 2A, which illustrate a portion of a structural element 10 having features that are commonly encountered in composite construction. The element shown is a blade-stiffened graphite/epoxy laminate structure having a blade stiffener 12 molded integrally with and extending generally perpendicularly from a skin panel 14. The cross section of this portion of the structural element is T-shaped, with the skin panel 14 defining the flange of the T and the blade 12 defining the web.

There are a number of well known techniques that may be used to fabricate the above-described structural element from uncured or unconsolidated composite materials. In one typical method, the structure is formed by positioning two L-shaped segments, each having a plurality of composite layers, in back-to-back relationship to form a T shape. The legs of the L-shaped segments that abut one another, i.e., the web of the T, form the stiffener. The other legs of the L-shaped segments are placed against the uppermost one of a group of layers that form the lower portion of the skin panel. The constituent layers curve smoothly through a 90-degree bend at the two corners 16 of the structure. The portion of the structure in the vicinity of the corners comprises what is known as the radius region, or radius 18.

Figures 2A, 2B:
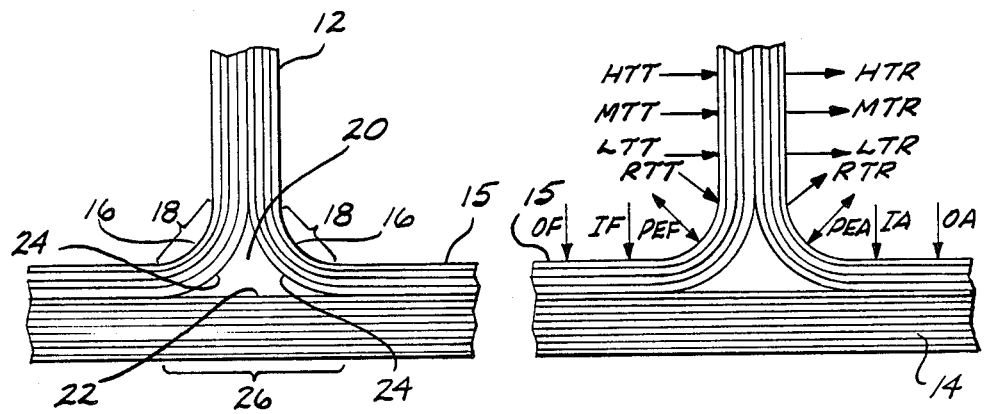
FIGS. 2A and 2B are pictorial cross-sectional views of the blade-skin intersection of the structure of FIG. 1 illustrating the sound patterns for inspecting this intersection.

As can be seen in FIG. 2A, the smooth bend in the layers that form the blade creates a cavity, or filler area 20, at the junction of the web and the flange of the T. The cross-sectional shape of the cavity 20 is substantially triangular, with the innermost surface of the lower skin segment defining the base 22 of the triangle, and the facing inner surfaces of the innermost L-shaped layers, which comprise the blade 12, forming the two concave legs 24 of the triangle.

Although not illustrated in FIGS. 1 and 2A, a fillet made of composite material and having a cross-sectional shape identical to that of the cavity 20 is fitted into the cavity. The structural element is then cured, during which process all of the layers and the fillet become integrally molded.

As briefly discussed above, flaws occurring in the blade/skin intersection can significantly reduce the strength of the composite structure. Of particular concern are voids within the filler area 20, delaminations along the base 22 or legs 24 thereof, and delaminations along the plies that form the blade in and adjacent the radius 18. Heretofore, there have been no reliable means for inspecting regions such as this in composite or other laminated structures. While hand-held ultrasonic through-transmission yokes can be used to inspect portions of the blade 12 and flange of the T, they do not lend themselves to inspection of the radius and the so-called "blade shadow" area 26. While it has been proposed to use contact pulse echo techniques to inspect the blade shadow areas, these proposals have not been satisfactory. In particular, the results of inspection with such techniques have not been reliable because of the complex construction of this region and the diverse and complex nature of the flaws that occur therein. As noted above, flaws such as delaminations typically follow the laminates or plies and, thus, occur in a direction that is generally normal to the page in the view of FIG. 2A. Because of this and because of the inherent tendency of the laminates and/or the fibers therein to act as waveguides, it is difficult to determine the location and size of flaws using past ultrasonic inspection techniques.

The present invention solves the problem of inspecting intersections in composite or other laminated structures, including radius areas in which the laminates curve and shadow areas where blades, webs, or other structures prevent straight, through-transmission inspection. This can be better understood with reference to FIG. 2B, which, in simplified pictorial form, shows one arrangement of ultrasonic transducers for inspection of the blade/skin intersection of FIGS. 1 and 2A. This arrangement generally comprises a plurality of ultrasonic transducers that are mounted in "shoes", i.e., transducer transport housings (not shown), that are engageable with the structure and mounted for synchronous translational movement therealong. The portion of the blade 12 adjacent the radius is inspected by three pairs of through-transmission transducers comprising three transmit transducers HTT, MTT, and LTT that are mounted in one shoe and three receive transducers HTR, MTR, and LTR, that are mounted in the other shoe and aligned with the transmit transducers HTT, MTT, and LTT, respectively. Four transducers OF, IF, IA, OA (two of which are mounted in each shoe) are operated in a loss-of-back mode, i.e., loss-of-back surface reflection mode, to inspect the portions of the skin panel 14 adjacent the intersection.

In accordance with an important aspect of the invention, two separate techniques are utilized to inspect the intersection region itself. For the first technique, an additional pair of transducers, RTT and RTR, provide a modified form of through-transmission inspection, referred to herein as "radius-to-radius" or "angular in/angular out" inspection in which sound is injected at an angle into the radius area on one side of the blade and received at an angle on the opposite of the blade. Preferably, both the radius-to-radius transmit transducer RTT and the radius-to-radius receive transducer RTR, are mounted in their respective shoes at the same angular orientation relative to the under-surface 15 of the skin panel 14.

Because of the complicated structure in this region, it is extremely difficult to precisely predict the manner and direction in which sound propagates through this region. It has been found, however, that a portion of sound that is injected at an angle into one of the radii propagates directly across the filler area. The radius-to-radius technique of the present invention utilizes this characteristic to inspect for flaws occurring in a region that extends through one of the radii, across the filler area, and out through the other radius. Although not essential to the invention, it has been found desirable to orient the radius-to-radius transmit transducer RTT and radius-to-radius receive transducer RTR at the same angle. The particular orientation selected for one or both of the transducers will, in a given situation, depend upon the configuration of the part being inspected. With this in mind, while a wide range of angular positions is contemplated by the invention, good results have been obtained in a prototype formed in accordance with the invention utilizing an angular orientation of 37.5 degrees for each of the transducers used for this modified through-transmission inspection.

The second of the two radius inspection techniques comprises pulse echo inspection at an angle through each of the two radii. To accomplish this "angular pulse echo" inspection, one of a separately operable pair of radius pulse echo transducers, PEF and PEA, is mounted in each of the shoes and oriented so as to transmit and receive sound along an axis that is at an angle relative to the undersurface 15 of the skin panel. A principle purpose of the pulse echo inspection provided by these transducers is to locate flaws occurring in the filler area 20. For a prototype formed in accordance with the invention to inspect a perpendicular blade/skin intersection, such s shown in FIG. 2B, an angular orientation of 45 degrees proved to be particularly desirable. Other angular orientations are, of course, possible within the purview of the invention and may be even more desirable for inspecting the area of intersection between other parts.

As noted above, a significant deficiency of prior systems has been an inability to indicate the size of a flaw in laminated structures. The transducer arrangement shown in FIG. 2B is specifically intended to overcome this problem. In particular, the transducers are arranged so that they may be energized in timed sequence to scan a given portion of the structure. For example, the scan may begin by first energizing the uppermost through-transmission transducers HTT and HTR and then successively energizing the remaining transducers in a sweeping manner down through the structure, concluding with energization of the two loss-of-back transducers OF and OA. The sequencing of the transducers in this manner effectively produces an ultrasonic scan in one direction (e.g., vertically downward) through the structure. Observance of the data obtained from adjacent transducers enables determination of the size of the flaw in the direction of the scan. By moving the transducer in another direction (e.g., normal to the plane of the drawing in FIG. 2B) and by repeating the scan sequence, additional samples of information concerning flaws may be obtained. By comparing the data obtained from scanning through adjacent cross sections of the part, it is possible to not only precisely located flaws, but also to size them in at least two dimensions.

Although the preceding paragraph and FIG. 2B suggests a linear array of transducers to scan a structure, it will be appreciated that the invention contemplates non-linear arrangements of transducers that can be energized in any order to obtain information concerning flaws in the structure. For example, in the preferred embodiment discussed hereinafter, a staggered array of transducers are utilized to avoid cross-talk and to allow the use of smaller volumes of coupling fluid.

Regardless of the arrangement of transducers, the aim is to position the transducers so that data may be taken simultaneously from a plurality of points (which data is later reconstructed to produce a "slice-like" image of the part). One way of accomplishing this is to manipulate the data with a computer and thereafter present it on a display or visual display or as printed output so that the person evaluating the inspection has the information presented as if the actual scan were taken in a sequence of staggered planes through the part.

There are many possible ways to configure shoes to position and transport transducers to carry out the technique just described. One particular arrangement for inspecting a similar T-shaped structure (the lower flange of an "I" stiffener) is discussed in detail below. As will become apparent from that discussion, it is generally preferable to stagger the transducers along the shoes in the direction of the scan rather than having the transducers all aligned, for example, in a given vertical plane. With the preferred arrangement, the information derived from each of the transducers of transducer pairs, i.e., presence, position, and size of flaw information, can be stored and electronically associated in accordance with the known timing of the energization sequence to "create" the desired skin-like inspection scan.

FIGS. 3A through 3D pictorially illustrate a manner in which the foregoing principles and one additional radius inspection technique can be combined to form an ultrasonic probe for inspecting a composite "I" stiffener. A detailed description of a probe embodying the techniques illustrated in FIGS. 3A through 3D appears below in connection with FIGS. 4 through 17F. Briefly, this probe comprises six shoes that are cooperatively arranged in two sets or assemblies. An upper flange/web shoe assembly has four shoes that carry transducers for inspecting the upper flange, the upper portion of the web, and the radius areas therebetween. The other two shoes are arranged as a lower flange/web shoe assembly and include transducers for inspecting the lower flange, the lower portion of the web, and the lower radius regions. FIG. 3E and FIGS. 18 through 20 corresponding thereto illustrate a toolside shoe that may be used in conjunction with the probe of FIGS. 3A through 3D (and 4 through 17F) to inspect the panel to which the stiffener is attached. The principal purposes of the toolside shoe are (a) to locate flaws, particularly delaminations occurring along base 22 of the filler area; and (b) to locate flaws in the outer skin.

Referring to FIG. 3A, a composite "I" stiffener 30 has an upper flange 32 at its free end, a web 34, and a lower flange 36, which is integrally molded with a skin panel 38. This structure is the same for FIGS. 3B through 3E and, although not shown, is to be understood as comprising an integrally molded laminated structure such as one formed from graphite/epoxy materials. In this regard, the intersection between the web 34 and lower flange 36 is substantially identical to the blade/skin intersection shown in FIG. 2A having two lower radii, 40 and 42, on either side of the web and a filler area (not shown). The upper flange is of similar construction, having a pair of upper radii, 44 and 46, on the underside of the flange and a filler area (also not shown) similar to that shown in FIG. 2A.

In many stiffened structures, the skin panel 38 will be quite large in dimension relative to the lower flange 36, making it difficult to arrange and manipulate inspection shoes on both sides of the structure so that through-transmission inspection of the lower flange and skin panel 38 may be accomplished in an economic manner. In these situations, inspection of the lower flange, lower web, and the intersection therebetween is accomplished using the through-transmission, loss-of-back, and radius inspection techniques discussed in conjunction with FIG. 2B for inspecting the blade/skin intersection.

Referring to FIGS. 3B, 3C, and 3D, the transducers used for this inspection are mounted in one or the other of a left lower flange shoe 48 or right lower flange shoe 50. These lower flange shoes are configured for complementary mating engagement with the "I" stiffener 30. As shown in FIG. 3C, inspection of the lower portion of the web 34 is provided by seven lower web transmit transducers, WLT1-7, and seven lower web receive transducers, WLR1-7, that are aligned in pairs in corresponding vertical order in the left lower flange shoe 48 and right lower flange shoe 50, respectively. As mentioned above, the pairs of transducers are preferably mounted at staggered positions in the direction normal to the view of FIG. 3C to avoid clearance problems.

Referring now to FIG. 3D, the left and right sides of the lower flange 36 are inspected utilizing twelve transducers LOB1-12 operated in a loss-of-back mode. Six of these flange loss-of-back transducers LOB1-6 and LOB7-12 are mounted in each of the left lower flange shoe 48 and right lower flange shoe 50, respectively, and arranged in staggered, spaced-apart relation outward from the web to provide full coverage of both sides of the lower flange 36.

With reference now to FIG. 3B, the lower web/flange intersection is inspected using two of the inventive radius inspection techniques discussed above. First, a radius-to-radius modified through-transmission inspection of the lower radii 40, 42, and the filler area of the lower web/flange intersection is performed by a lower radius transmit transducer, L37.5T, mounted in the right lower flange shoe 50 and an associated lower radius receive transducer, L37.5R, mounted in the left lower flange shoe 48. The lower radius transmit transducer L37.5T injects sound at an angle, preferable 37.5 degrees, into the lower radius 42 and the portion of that sound that propagates through the structure and out the lower radius 40 is picked up by the lower radius receive transducer, L37.5R, which is similarly mounted at an angle (preferably 37.5 degrees) relative to the upper surface of the lower flange 36. Second, an angular pulse echo inspection of the lower radii 40, 42, and the filler area therebetween is performed by a left lower radius pulse echo transducer LL45P and a right lower radius pulse echo transducer RL45P, respectively. These transducers are arranged and operated in the same manner as the radius pulse echo transducers PEF and PEA of FIG. 2B, i.e., each transmit and receives sound along an axis that is at an angle (preferable 45 degrees) relative to the upper surface of the lower flange 36.

Inspection of the upper flange 32 and the upper portion of the web 34 is accomplished by transducers mounted in four shoes that are spring-loaded together to form an upper flange/web shoe assembly that clamps about these portions of the structure. The arrangement of the transducers in the four constituent shoes of this assembly is shown in FIGS. 3A, 3B, and 3C, which represent three separate cross-sectional views through these shoes. Specific details of the construction of these shoes are discussed below n conjunction with FIGS. 4 through 17F. For the present overview of this assembly, it is sufficient to note that the upper flange/web shoe assembly 62 (see FIG. 4) comprises a left upper flange shoe 52, a right upper flange shoe 54, a left top shoe 56, and a right top shoe 58. Since the opposed sides of each of the two sides of the upper flange 32 and the upper portion of the web 34 are readily accessible, it is possible to use through-transmission inspection techniques for these portions of the structure. For this purpose, six left upper flange transmit transducers LUFT1-6 mounted in the left top shoe 56 and six corresponding left upper flange receive transducers LUFR1-6 mounted in the left upper flange shoe 52 provide through-transmission inspection at spaced-apart locations on the left segment of the outer flange 32. Inspection of the right segment of the upper flange is accomplished in an identical manner by six right upper flange transmit transducers RUFT1-6 mounted in the right top shoe 58 and six right upper flange receive transducers RUFR1-6 mounted in aligned relationship therewith in the right upper flange shoe 54.

As illustrated in FIG. 3C, the upper portion of the web 34 is inspected using three spaced-apart pairs of through-transmission transducers. Sound is injected into the left side of the web by upper web transmit transducers WUT1-3 mounted in the left upper flange shoe 52 and is received by upper web receive transducers WUR1-3 mounted in the right upper flange shoe 54.

It will be appreciated from the description so far that an inspection of the web/outer flange intersection, including the two upper radii 44 and 46, can be accomplished with the single-sided radius inspection technique used for the web/lower flange intersection, i.e., pulse echo at an angle into each of the upper radii 44 and 46 and angular in/angular out modified through-transmission from the radius on one side of the web to the radius on the other side using transducers mounted in the underflange portions of the two upper flange shoes, 52 and 54. While this approach is possible, it has been found that better, more consistently reliable results can be achieved using the modified approach shown in FIG. 3B. In this arrangement, the radius-to-radius through-transmission inspection is retained and provided by a pair of transducers mounted in the left and right upper flange shoes 52 and 54. Sound is injected into the upper radius 44 by a first upper radius transmit transducer U37.5T carried by the left upper flange shoe and, after exiting the opposite radius 46, is picked up by a first upper radius receive transducer U37.5R mounted in the right upper flange shoe 54.

Since it is possible to simultaneously engage both the upper (top) and lower (bottom) surfaces of the outer flange 32, it is possible and desirable to utilize yet another modified form of through-transmission inspection of the critical radius and filler regions. As discussed above, this technique is referred to herein as "normal in/angular out through-transmission inspection," "flange-to-radius inspection," or "double-sided radius inspection" and comprises, generally, the injection of sound at a predetermined angle into the top of the upper flange 32 and the receipt of portions of that sound by transducers that are in predetermined angular alignment with the lower surface of the upper flange 32. For this purpose, a right upper radius transmit transducer RU45T is mounted in the right top shoe 58 and injects sound into the top of the upper flange 32 in a direction that is in general vertical alignment with the web 34. A portion of the sound so injected propagates through the filler area and out through the upper radius 46 and is received by a right upper radius receive transducer RU45R that is mounted in the right upper flange shoe 54. Although not illustrated in FIG. 3B, the left top shoe 56 includes a left upper radius transmit transducer LU45T (see FIG. 5) to inject the sound into the top surface of the outer flange 32 in a direction that is generally vertically aligned with the left side of the web 34. Portions of the sound so injected by this transducer propagate through the filler area, and out through the radius 44 where they are received by a left upper radius receive transducer LU45R as shown in FIG. 3B.

It is to be noted that the two upper radius transmit transducers and their respective upper radius receive transducers can be operated in a reverse mode. That is to say, the function of these transducers can be reversed so that the transducers mounted in the left and right upper flange shoes 52 and 54 can be made operable to inject sound at a predetermined angle, which may vary over a wide range but which is preferable 45 degrees, into the respective radius 44 or 46 into which it is directed. Portions of the sound so injected would then propagate through the radius, the filler area, and out through the top surface of the upper flange 32 where they would be received by the aligned receive transducer mounted in the top shoe 56 or 58.

A similar reversal of functions, or direction of sound transmission, could also be effected for the left and right upper flange receive and transmit transducers shown in FIG. 3A so that the sound would be directed into the lower surface of the flange 32 by transducers mounted in the shoes 52 and 54, and received at the top surface of the upper flange by transducers mounted in the shoes 56 and 58.

Figure 7:
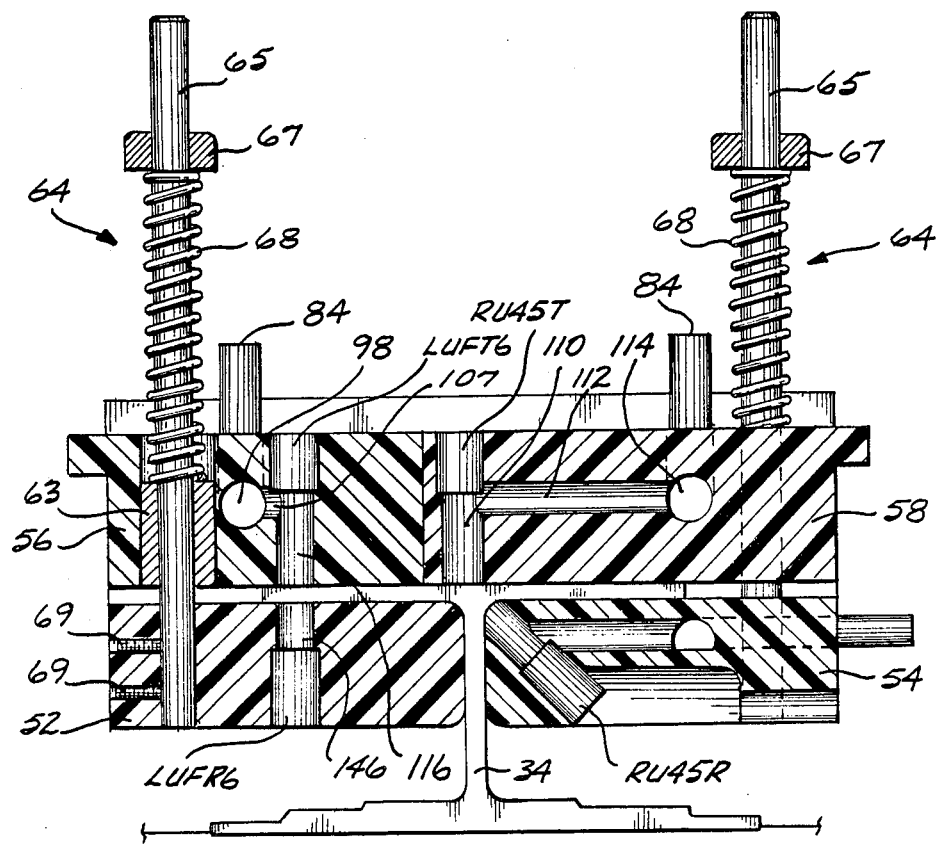
FIG. 7 is a cross-sectional front elevational view taken along line 7—7 of FIG. 5.

As will be discussed in greater detail in conjunction with FIG. 7, the two upper radius transmit transducers LU45T and RU45T are oriented generally perpendicular to the top surface of the outer flange 32 and positioned in predetermined alignment with the side of the web 34 on which its associated receive transducer is positioned. The effect of this arrangement is to provide two angled ultrasonic beam paths that intersect one another at angles to provide coverage of both the radius area as well as the filler region. In this regard, it is to be appreciated that the two transmit transducers RU45T and LU45T are positioned over the base of the triangular cavity in the outer flange/web intersection and, thus, provide information concerning delaminations occurring in this area.

To inspect for defects from the toolside, i.e., the side opposite the stiffener, an additional toolside shoe 60 is provided. For the examination of a structure having a large skin panel 38, it is generally economically advantageous to have the toolside shoe 60 manipulated independently of the shoe assemblies utilized to inspect the stiffener and adjacent skin surfaces on the opposite sides of the panel. As will be discussed in greater detail with reference to FIGS. 18 through 20, the toolside shoe 60 includes 16 pulse echo transducers that are arranged in a matrix and operate in a loss-of-back mode.

Reference is now made to FIG. 4 for a more detailed description of the probe illustrated in FIGS. 3A through 3D. The structure shown under inspection is the same as in FIGS. 3A through 3E, having an "I" stiffener integrally molded with a skin panel 38. The upper flange 32 and upper portion of the web 34 of this structure are inspected by an upper flange/web shoe assembly 62 consisting of the left and right top shoes 56 and 58, respectively, and the left and right upper flange shoes 52 and 54, respectively. Each of the left and right top shoes 56 and 58 is spring-loaded against the top of the upper flange 32 by two top spring assemblies 64 that are anchored at their lower ends in the left and right upper flange shoes 52 and 54 as shown in greater detail in FIG. 7. The two upper flange shoes, 52 and 54, are, in turn, spring-loaded against the upper portion of the web 34 and the lower surface of the upper flange 32 by a pair of flange spring assemblies 66, which are shown in greater detail in FIGS. 5 and 8.

To inspect the lower portion of the web 34, the lower radii 40, 42, lower flange 36, and the portions of the skin panel 38 thereunder, the left lower flange shoe 48 and the right lower flange shoe 50 are cooperatively arranged in aligned relationship on opposite sides of the web as a lower flange/web shoe assembly. Each of these shoes is held in engagement with the web and lower flange by a support assembly that includes a rod 70, a compression spring 72, and a block 74. Each of the blocks 74 contain two linear bearings that slidably receive the rod 70. The compression spring 72 is held in a state of compression between the linear bearing and a collar 76 that is fastened to the rod. To ensure proper engagement between the shoes and the stiffener 30 and to accommodate structures of different shape and configuration, the lower end of each rod 70 is pivotally connected to its respective lower flange shoe 48, 50 and each of the linear bearings 74 is pivotally connected to a scanner platform 78. With this arrangement, it will be seen that, as the scanner platform is moved along the structure, the two lower flange shoes are maintained in floating, spring-biased engagement with the stiffener.

The upper flange/web shoe assembly 62 is also connected to the scanner platform 78 so that it is moved along the stiffener in synchronism with the movement of the two lower flange shoes. Since the upper flange/web shoe assembly includes its own spring assemblies 64 and 66 to hold the constituent shoes together and in engagement with the stiffener, connection to the scanner platform can be made with a single rod 80 that is pivotally connected at one end to the platform and at the other end to the left upper flange shoe 52. It will here be observed that the arrangement of FIG. 4 illustrates considerations that go into the design of the probe and the structure that holds the probe in place against that part to be inspected, such structure being herein referred to as a "probe holder." Where the shape of the structure (such as the illustrated flange on an "I" stiffener) permits ready access to the radius and blade (or web) shadow areas, it is possible to configure a self-supporting probe such as the upper flange/web shoe assembly 62 that holds itself against the part such that the ultrasonic transducers are maintained in proper alignment with one another and with the areas under inspection. Such a self-supporting arrangement complicates the shoe design but simplifies the design of, or the connection to, the probe holder.

The arrangement of the left and right lower flange shoes 48 and 50 and the associated support assemblies that hold the shoes to the scanner platform 78 illustrate the opposite situation, where a simpler probe design requires a more complicated probe holder. A principal reason for this approach is that the presence of the physically large skin panel 38 makes it practically difficult to perform a double-sided inspection of the two lower radii 40 and 42 and the filler region therebetween. Consequently, a single-sided inspection technique is used for these areas, with a subsequent inspection thereof being made from the opposite side using a separate probe such as the one illustrated in FIGS. 18 through 20 discussed below. It is to be appreciated that one advantage of the arrangement just described is that the mechanisms that hold the probes, as well as the mechanism that transports the same relative to the part, may be relatively simple. As will be discussed in conjunction with the alternative embodiment of FIGS. 21 through 23, it is possible, and particularly desirable in a production mode, to alter the design of the shoes and the manner in which they are held together so that the resultant probes have a plurality of degrees of freedom of movement.

Referring again to FIG. 4, the right upper flange shoe 54, the left top shoe 56, and the right lower flange shoe 50 are each shown to have a water supply hose designated "H" and an electrical lead designated "L" running thereto. These elements are intended to pictorially illustrate that there is an electrical connector running to each of the transducers in each of the blocks and a plurality of hoses through which water is supplied to (and then through) internal conduits within the shoes to provide coupling between the transducers and the part under inspection. The specific details of these arrangements will become apparent in the ensuing description.

Figure 5:
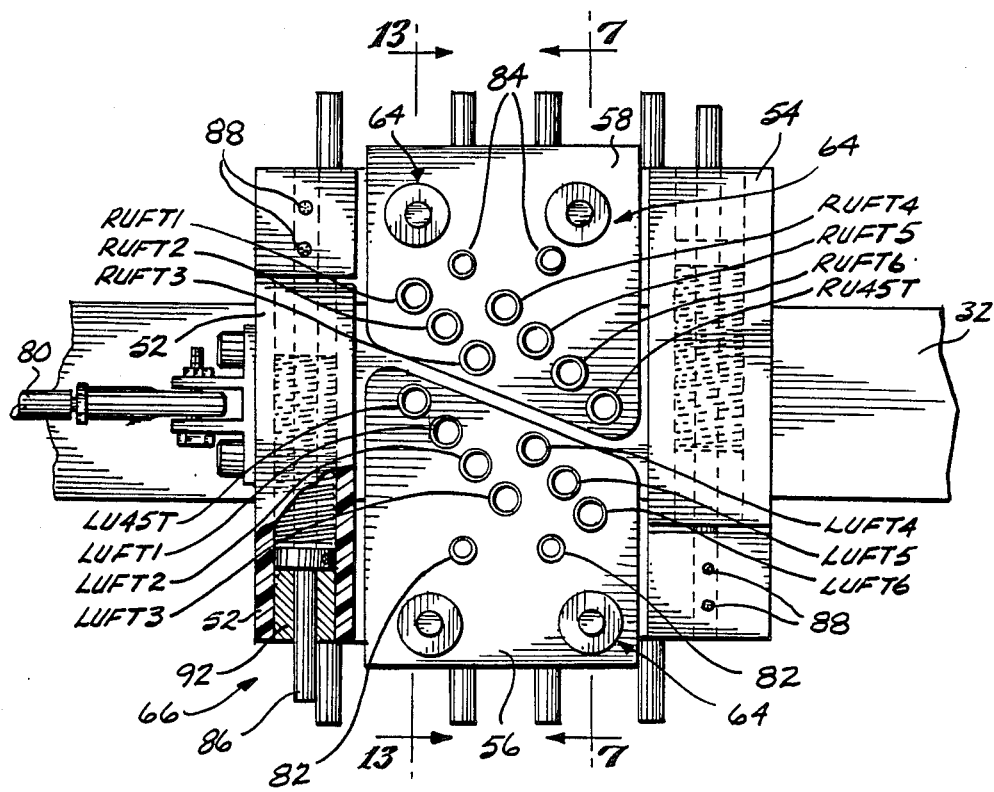
FIG. 5 is a plan view with parts broken of the probe of FIG. 4.

Referring now to the plan view of FIG. 5, the left top shoe 56 and right top shoe 58 each include seven ultrasonic transducers that are used in a transmit mode. The six left upper flange transmit transducers LUFT1-6 are mounted in spaced-apart relation to one another and oriented so as to be substantially normal to the upper flange 32 of the "I" stiffener. Each of these transducers operates as described in conjunction with FIG. 3A to transmit sound to the one of the left upper flange receive transducers LUFR 1-6 with which it is aligned. As discussed in relation to FIG. 3B, the left upper radius transmit transducer LU45T is also mounted so as to be substantially normal to the outer flange 32 and aligned to inject sound that propagates through the upper radius 44 where it is received by the left upper radius receive transducer LU45R mounted in the left upper flange shoe 52. Water for coupling the sound of the seven receive transducers in the left top shoe 58 is supplied to internal conduits through a pair of water inlets 84 (see FIG. 10).

The right top shoe 58 has the same configuration as the left top shoe, having six right upper flange transmit transducers RUFT1-6 mounted in an array and oriented such as to be substantially normal to the top surface of the upper flange 32 and aligned with a respective one of the right upper flange receive tranducers RUFR1-6. Although the left and right top shoes are constructed identically, in the assembled probe, the right top shoe is rotated 180 degrees relative to the left top shoe. As described previously, the right upper radius transmit transducer RU45T is also oriented to be substantially perpendicular to the top surface of the upper flange 32 and positioned to transmit sound that travels through the upper radius 46 to the right upper radius receive transducer RU45R mounted in the right upper flange shoe 54. Referring for a moment to FIG. 7, it will be seen that one edge of the right upper radius transmit transducer RU45T is in line with the side edge of the web on which its associated receive transducer RU45R is located. Although not shown in the FIGURES., the left upper radius transmit transducer LU45T is aligned in the same manner with the opposite side of the web 34, i.e., the side edge of the web on which the left upper radius receive transducer LU45R is located.

The right top shoe 58 also includes a pair of water inlets 84 that communicate with a network of supply conduits and delay lines that couple the sound from the part to the receive transducers. Further details of these water lines are illustrated and described elsewhere, particularly in FIG. 10.

As briefly discussed above, two sets of spring assemblies 64, 66 join the top shoes and upper flange shoes together into a self-supporting assembly that clamps onto the upper flange 32 and the upper portion of the web 34. Several benefits flow from this arrangement. First, the shoes remain in tight engagement with the part under inspection such that the transducers (particularly those in the radius) remain properly positioned. Second, since the resultant assembly (probe) is self-supporting, an uncomplicated, relatively inexpensive structure can be used to hold and transport the same.

Figure 8:
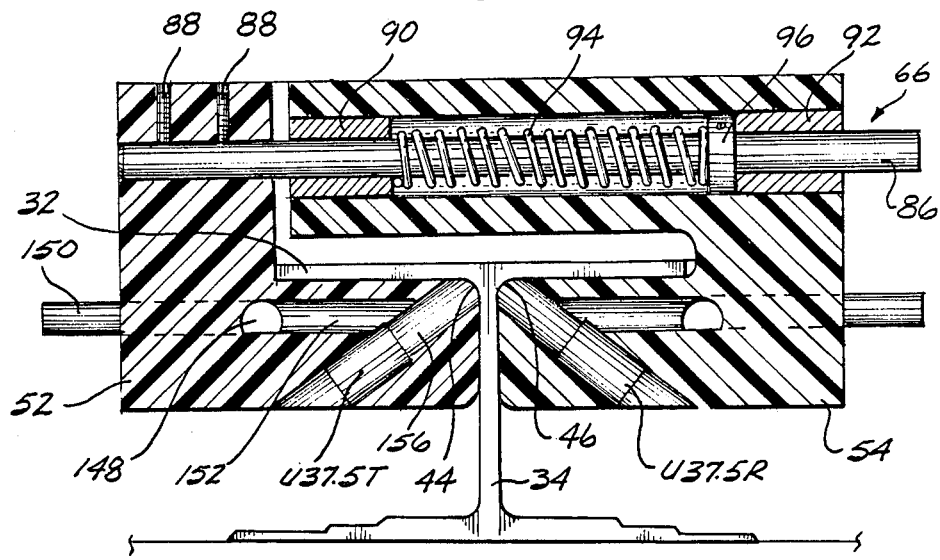
FIG. 8 is a cross-sectional front elevational view taken along line 8—8 of FIG. 6.
Figure 11:
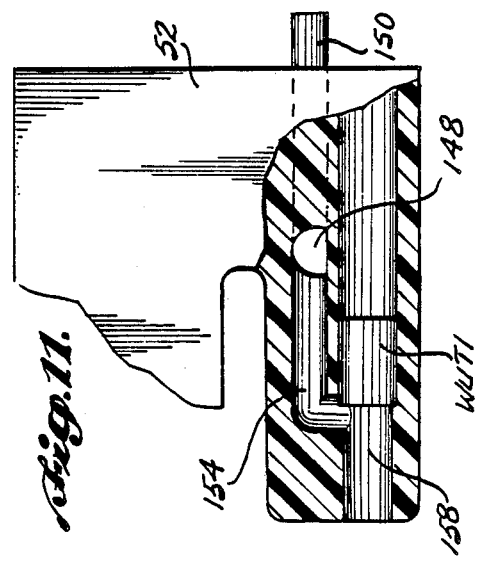
FIG. 11 is a front elevational view of the left upper flange shoe of the upper flange/web shoe assembly of FIG. 4, with parts broken to show the position of the forwardmost transducer and the water passage therefor.
Figure 12:
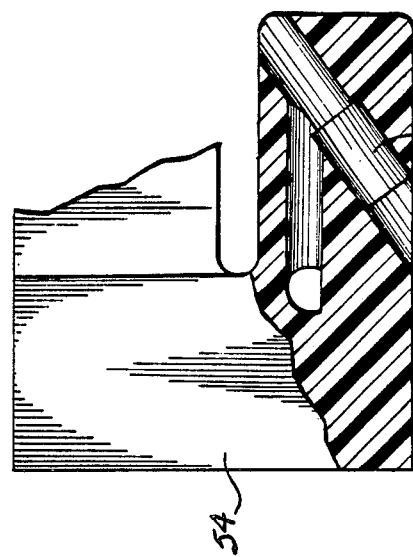
FIG. 12 is a front elevational view of the right upper flange shoe of the upper flange/web shoe assembly of the probe of FIG. 4, with parts broken to show the forwardmost transducer and the water passage therefor.

Considering now the details of the spring assemblies, the two upper flange shoes 52 and 54 are biased toward one another so as to resiliently clamp the upper portion of the web 34 therebetween by two identical flange spring assemblies 66. With reference to FIGS. 5 and 8, each of these spring assemblies includes a rod 86 that is anchored at one end in an upstanding post portion of one of the upper flange shoes (the left upper flange shoe 52 in FIG. 8) by a pair of screws 88. The rod passes through two bushings 90 and 92, contained within a bore formed within an extension in the opposite flange shoe (right upper flange shoe 54 in FIG. 8). A spring 94 is held in a state of compression between bushing 90 and a retainer collar 96 that is secured in a fixed position to the rod 86. Since the spring bears against the bushing 90, and since the rod slides in the two bushings 90, 92, there exists a spring force that urges the right upper flange shoe 54 toward the left upper flange shoe 52, forcing the underflange portion of these two shoes into engagement with the web 34. These portions of the shoes are configured complementary to the configuration of the portions of the upper flange, web 34, and upper radii 44, 46 so that there is a complementary mating engagement that ensures the proper spacing of the transducers from the areas being inspected and continuity of the trapped volume of coupling liquid.

As shown in FIG. 5, the second flange spring assembly 66 is received in a bore formed in an upper arm portion of the left upper flange shoe 52 that extends over the upper flange 32 of the "I" stiffener. The arrangement and operation of this flange spring assembly are identical to that of the flange spring assembly just discussed, with one end of the rod 86 being securely fastened by screws 88 to an upstanding post portion of the right upper flange shoe 54.

Four identical top spring assemblies join the top shoes 56 and 58 to the flange shoes 52 and 54. As seen best in FIG. 7, each of those top spring assemblies 64 includes a rod 65 that is suitably secured at its lower end in one of the upper flange shoes 52 or 54 as, for example, by screws 69. Each of the top shoes has a bushing 63 that is mounted in a bore thereof. A spring 68 is held in compression between the bushing 63 and a collar 67 that is attached in a fixed position to the rod 65. Since the bushing 63 is free to slide along the rod 65, the spring forces draw the top shoes and upper flange shoes associated therewith toward one another.

Figure 6:
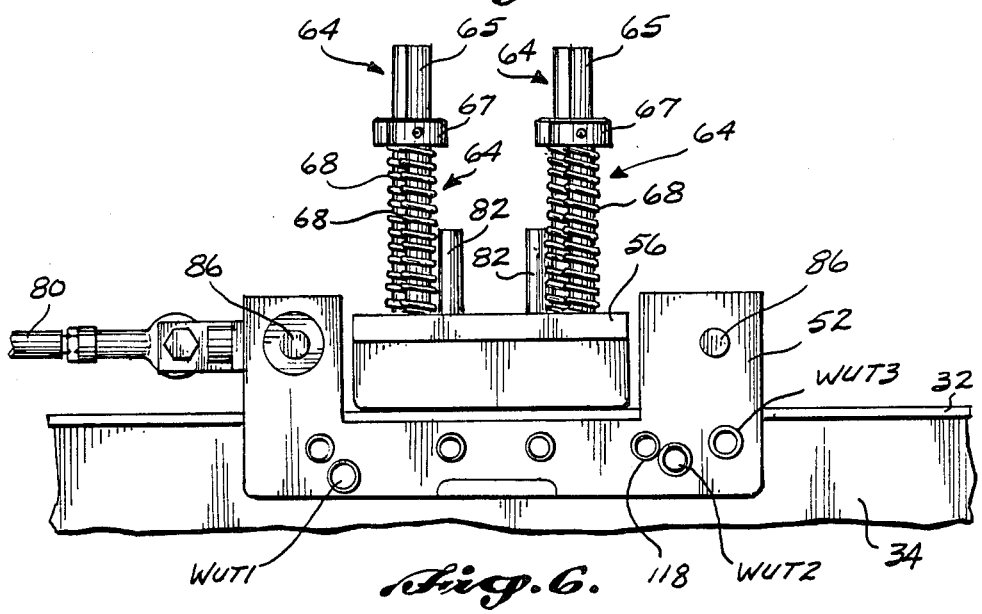
FIG. 6 is a left side elevation view of the probe of FIG. 4.

As previously discussed in relation to FIG. 3C, a through-transmission inspection of the upper portion of the web is made by the three transmit transducers WUT1-3 mounted in the left upper flange shoe 52 and their associated receive transducers WUR1-3, mounted in the right upper flange shoe 54. Referring to FIG. 6, the three transmit transducers are mounted at spaced-apart vertical intervals so as to inspect different vertical regions of the web 34. These transducers are also positioned so as to be spaced apart from one another in the direction of scan (right to left in FIG. 6). These transducers are also positioned on either side of a central region of the shoe that contains the seven receive transducers (LUFR1-6 and LU45R) that are aligned with their counterpart transmit transducers (LUFT1-6 and LU45T) that are mounted in the left top shoe 56.

The three upper web receive transducers WUR1-3 are mounted on the opposite side of the web at positions in the right upper flange shoe 54 that mirror the locations of their respective transmit transducers WUT1-3. This mirror relationship holds true for all of the various aligned pairs of transducers in all of the shoes. Three principle design objectives underlie the overall arrangement of transducers. First, the transducers are staggered so as to provide as full coverage as possible of the portion of the part that they inspect. Secondly, the transducers are positioned adjacent one another in a pattern that enables the creation of a scan through the part so that flaws may be not only located, but sized. Finally, the transducers are positioned in spaced relation to one another and to the stiffener so as to enable the simultaneous energization of selected pairs of transducers while at the same time avoiding channel-to-channel interference.

FIGS. 7 through 13 illustrate in greater detail the precise orientation of exemplary pairs of tranducers in the upper flange/web shoe assembly and the conduits and delay lines used to supply water as the ultrasonic coupling medium. To simplify the visual presentation, the electrical connections to the transducers and the hoses that attach to the various inlet tubes have been omitted from these FIGS. and from most of the remaining drawings.

FIG. 10 illustrates the overall arrangement of tranducers and water passageways in the left top shoe 56 and the left upper flange shoe 52. From the discussions above, it will be readily understood that the arrangement of transducers, supply lines, and delay lines in the right top shoe 58 and right upper flange shoe 54 closely resembles the arrangement shown in FIG. 10 for the left top shoe 56 and the left upper flange shoe 52, respectively. In particular, the four transducers U37.5T, WUT1, WUT2, and WUT3 and their associated supply lines and delay lines are mirrored in the right upper flange shoe 54. In addition, the transducers and associated water passageways in the right upper flange shoe 54 are rotated 180 degrees relative to their counterparts in the left upper flange shoe 52. Finally, the arrangement of transducers and passageways in the right top shoe 58 are rotated 180 degrees relative to the arrangement illustrated in FIG. 10 for the left top shoe 56.

In the left top shoe 56, two water inlets 84 receive water through hoses (not shown) and supply the same to a central channel 98. From the central channel, water is supplied separately to each of the transmit transducers LU45T and LUFT1-6 through branch channels 101 through 107. Each of the branch channels opens at the face of its respective transmit transducer into a delay channel, which extends from the face of the transducer to an opening on the underside of the left top shoe. Although not shown in the FIGS. the delay channels for each of the transducers are identical to delay channel 108 shown in FIG. 10 for the left upper radius transmit transducer LU45T. The specific configuration of this delay channel will be readily understood from FIG. 7, which illustrates the delay channel 110 for the transmit transducer RU45T in the other shoe, i.e., in the right top shoe 58. Recalling the 180 degrees rotated arrangement of transducers and water supply passageways in the top shoes, the correspondence between the branch channel 112 and the central channel 114 in right top shoe 58 with the branch channel 101 and central channel 98 in the left top shoe 56 will be understood. The common construction of the delay channels and the water passageways in the two top shoes will be further appreciated from the illustration in FIG. 7 of the arrangement and connections between the water inlet 84, central channel 98, branch channel 107, and delay channel 116 for the left upper flange transmit transducer LUFT6 in the left top shoe 56.

Figure 9:
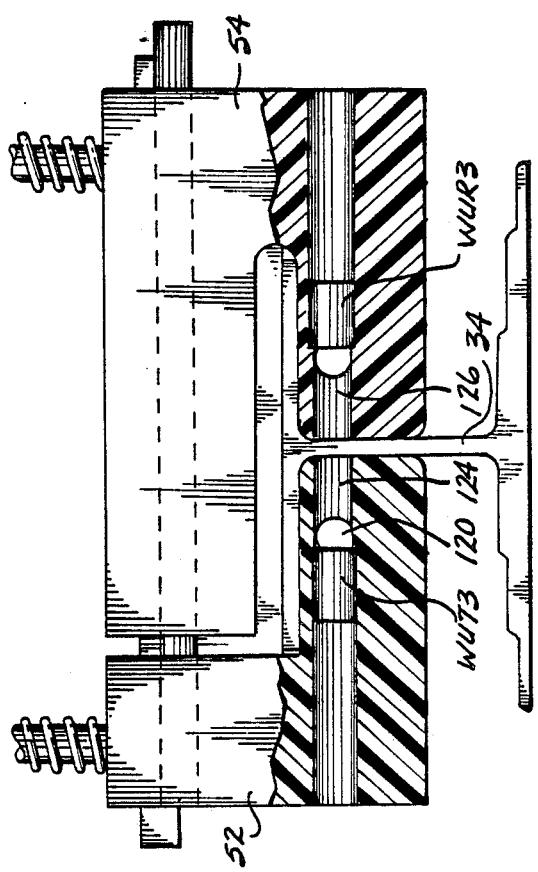
FIG. 9 is a rear elevational view, with parts broken, of the probe of FIG. 4.
Figure 13:
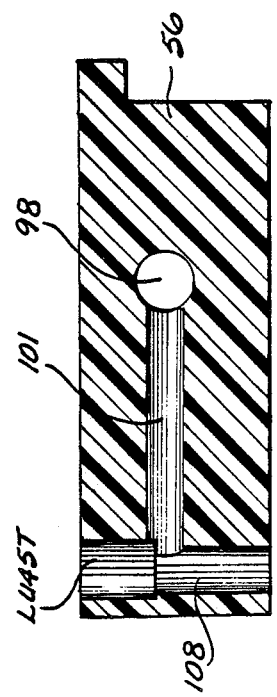
FIG. 13 is a cross-sectional view of the left top shoe of the upper flange/web shoe assembly of the probe of FIG. 4 taken along line 13—13 of FIG. 5.

Referring again to FIG. 10, the transducers in the left upper flange shoe 52 are arranged in groups for purposes of water supply. In the front of the shoe, the two upper web transmit transducers WUT2 and WUT3 are supplied water through an inlet channel 118 and a connecting channel 120. The connecting channel opens at the face of the transducers WUT2 and WUT3 into respective delay channels 123 and 124, respectively. As shown in FIG. 9, each of the delay channels 124 (and 123, not shown) extends from the face of the transducer to an opening on the inner face of the left upper flange shoe 52. An identical arrangement exists in the front of the right upper flange shoe 54 with the web upper receive transducers WUR2 and WUR3 having separate delay channels that are supplied via a common connecting channel and an inlet channel. FIG. 9 illustrates the manner in which the web transmit and receive transducers (here WUT3 and WUR3) and their respective delay channels 124 and 126 are aligned to establish an ultrasonic path for inspecting the web 34 of the stiffener.

The central portion of the left upper flange shoe 52 contains the seven receive transducers, LU45R and LUFR1-6 that are cooperatively arranged for ultrasonic communication with their associated transmit transducers LU45T and LUFT1-6, respectively, in the left top shoe 56. These seven receive transducers receive their supply of coupling water along individual branch channels 128 through 134, which are each connected with a central channel 136. The central channel is, in turn, fed through a pair of inlet channels 138 that open on the side of the flange shoe. The left upper radius receive transducer LU45R is ultrasonically coupled into the upper radius 44 by a delay channel 140 that is connected to the branch channel 128 and that extends from the face of this transducer to an opening along the rounded edge of the left upper flange shoe 52. The left upper flange receive transducers have individual delay channels 141 through 146 that extend from the face of the transducers to openings on the flat upper surface of the left upper flange shoe 52 that mates with the flat undersurface of the left top shoe 56. Each of the delay channels 140 through 146 is connected adjacent the face of its associated transducer with a particular one of the branch channels 128 through 134.

At the rear of the left upper flange shoe 52, the upper web transmit transducer WUT1 and the upper radius transmit transducer U37.5T are commonly grouped for water supply from a connecting channel 148 that is, in turn, supplied through an inlet channel 150. In particular, the transducer U37.5T is supplied through a branch channel 152 that connects at one end to the channel 148 and that opens at the other end adjacent the face of the transducer. Ultrasonic coupling of transducer U37.5T to the upper radius 44 is provided through a delay channel 156. This delay channel extends from the face of U37.5T to an opening along the rounded edge of the left upper flange shoe 52, as shown in greater detail in FIG. 8. The transducer WT1 is coupled to the upper portion of the web through a delay channel 158 that connects adjacent the face of that transducer with a branch channel 154 that communicates with the connecting channel 148, as shown in detail in FIG. 11.

With the foregoing arrangement, and as a result of the conforming engagement of the shoes with the web and outer flange, it is possible to maintain trapped volumes of coupling liquid with only intermediate flow rates.

FIGS. 14 through 17E illustrate the details of the left and right lower flange shoes 48 and 50. As discussed above in conjunction with FIGS. 3B, 3C, and 3D, these shoes perform a "single-sided" inspection of the lower portion of the web 34, the lower flange 36, the lower radii 40 and 42, and the filler region therebetween. In particular, the web is inspected using a through-transmission technique; the lower flange is inspected using a pulse echo loss-of-back technique; and the radius and filler regions are inspected using both a pulse echo technique and a radius-to-radius modified through-transmission technique.

Before discussing the detailed arrangement of these transducers, it will again be observed that the design decision to use a single- rather than double-sided approach is dictated by the presence of a large skin panel 38 attached to the stiffener. In particular, it is practically and economically difficult to position, move, and maintain alignment between shoes on opposite sides of a large skin panel.

Figure 14:
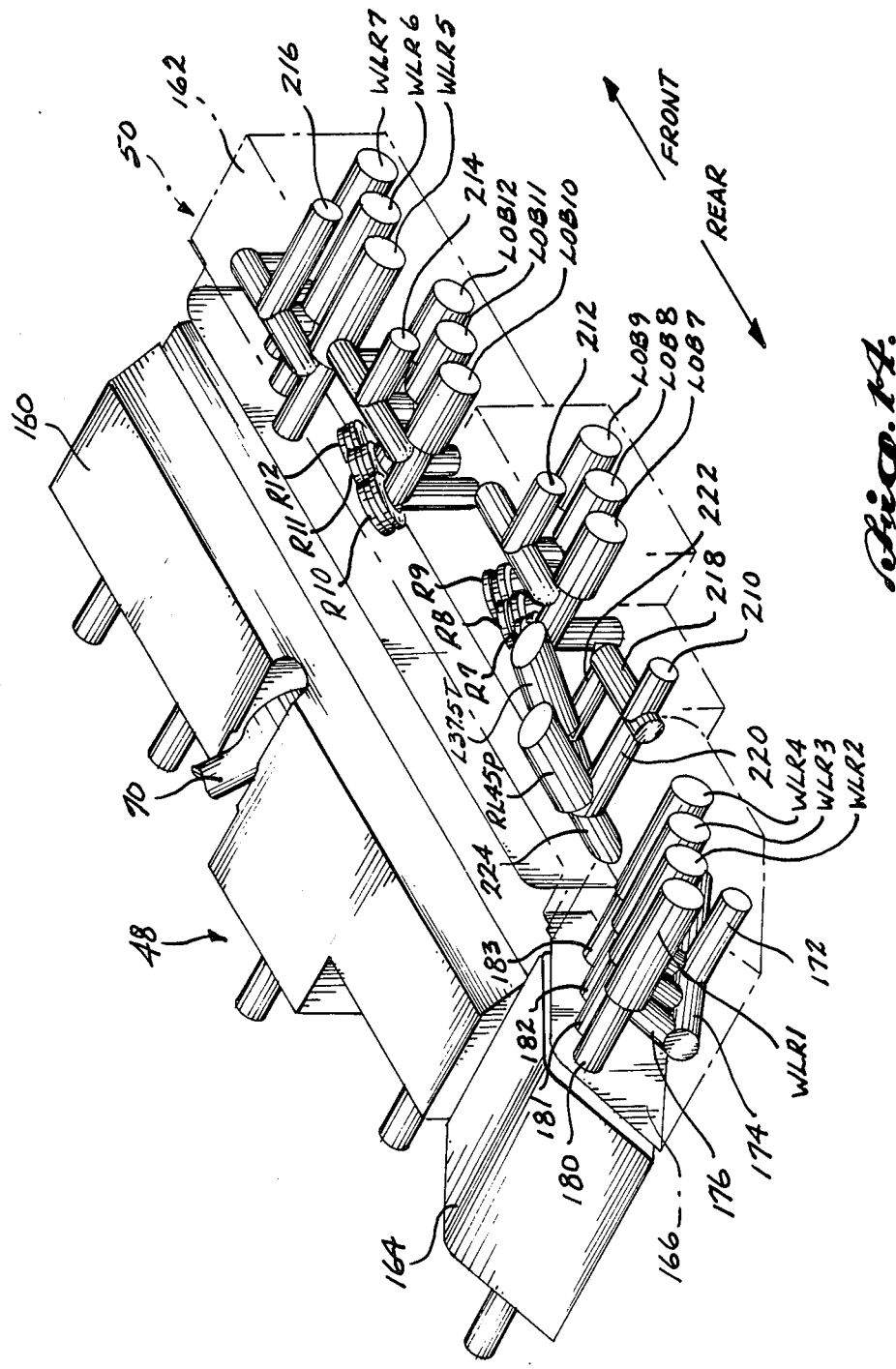
FIG. 14 is a simplified, isometric view, with parts removed, of the lower flange/web shoe assembly of the probe of FIG. 4 illustrating the positioning of the transducers, reflectors, internal water passages and delay lines in the right lower flange shoe.

Referring now to FIGS. 14 through 16, the two shoes 48 and 50 are symmetrically configured for alignment with one another and for mating engagement with the lower portion of the web and the flange of the stiffener. The shoes 48 and 50 have main blocks 160 and 162, respectively, and extension blocks 164 and 166, respectively. The extension blocks are pivotally mounted to their respective main blocks so that the transducers mounted therein can be moved vertically to accommodate webs of varying height. As shown in FIGS. 15 and 16, this pivotal connection consists of a pin 168 that passes through bores formed in two projections on the extension block 164 and two projections on the main block 160. A spring 170 maintains a bias that urges the extension block 164 into its most vertical position. Although not illustrated in the FIGS., the same arrangement is used to provide pivotal connection between the extension block 166 and the main block 162 of the right lower flange shoe 50.

Mounted in the extension block 164 are four of the seven lower web transmit transducers WLT1-4 that are used to inspect the web 34. The four lower web receive transducers WLR1-4 that complete these through-transmission pairs are mounted in the extension block 166 so as to be in alignment with their respective send transducer. An identical arrangement of conduits is used in each of the two extension blocks to supply water that couples the transducers to the part under inspection. As shown in FIG. 14, and inlet 172, which is connectable via a hose, not shown, to a supply of water, is connected to a central channel 174. An individual branch channel extends from the central channel 174 to the face of each of the transducers. In FIG. 14, only the branch channel 176 leading to the receive transducer WLR1 is designated. Again, recalling the symmetry between the two lower flange shoes 48 and 50, the arrangement of the individual branch channels will be readily understood from FIG. 15, which shows the branch channels leading from the central channel 178 to each of the transmit transducers WLT1-4. Referring again to FIG. 14, branch channels 180 through 183 extend from the face of the lower web receive transducers WLR1-4 to openings provided on the inner face of the extension block 166 that engages the web.

The main blocks 160 and 162 carry the remaining three pairs of transducers that provide through-transmission inspection of the web, 12 transducers (six in each shoe) that perform loss-of-back inspection of the lower flange 36, and four transducers that perform the radius-to-radius and angular pulse echo inspection of the junction region between the lower flange and the web. Referring to FIG. 15, the three lower web transmit transducers WLT5-7 are mounted in the front portion of the main block 160 in staggered vertical and horizontal relationship to one another. The six flange loss-of-back transducers LOB1-6 are mounted in a similar staggered relationship in the central portion of the main block on either side of the point at which the transport rod 70 is pivotally connected to the main block.

The loss-of-back transducers are mounted in the illustrated horizontal arrangement to minimize the required vertical dimension of the main block 160 and to enable placement of the transducer wires on the "free" side surface of the main block where they will not interfere with or otherwise contact the part under inspection.

Figures 17A, 17D:
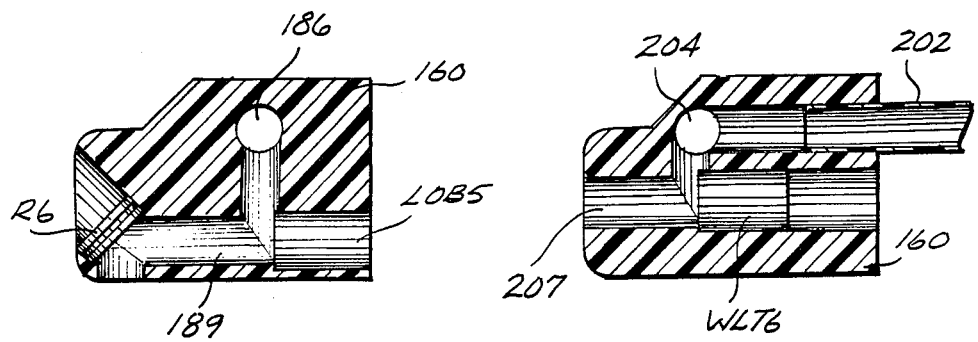
FIGS. 17A through 17F are rear elevational cross-sectional views taken along lines 17A—17A, 17B—17B, 17C—17C, 17D—17D, 17E—17E, and 17F—17F, respectively, of FIG. 15.
Figures 17B, 17E:
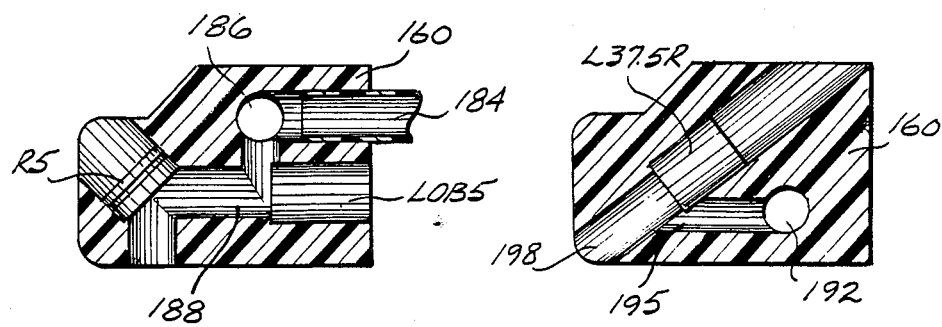
Figures 17C, 17F:
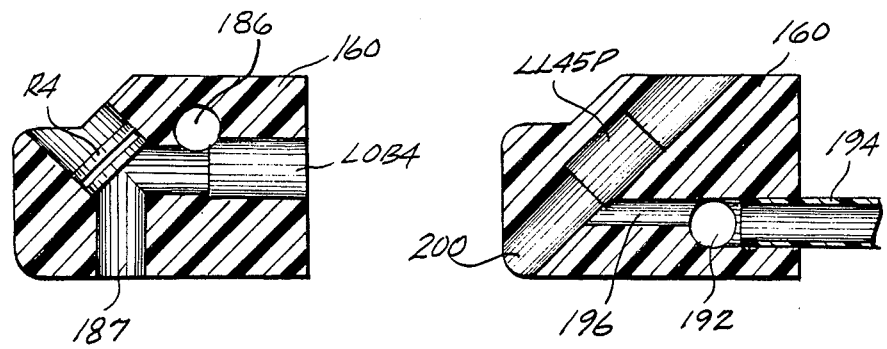
Figure 19:
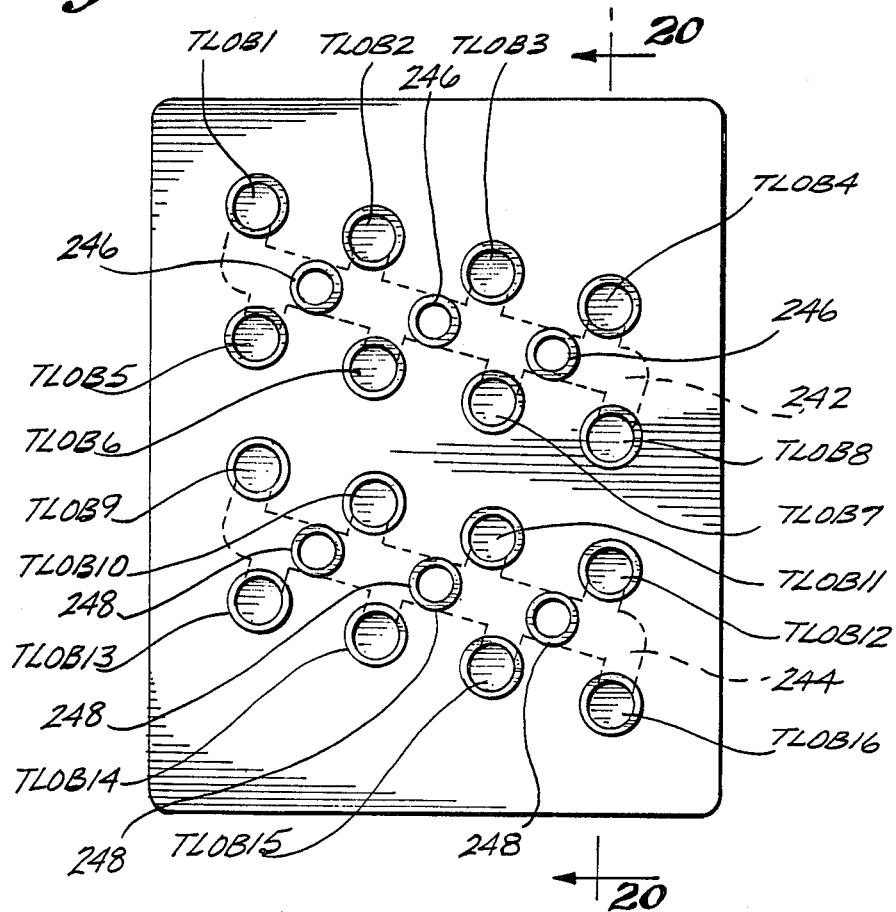
FIG. 19 is a plan view of the toolside shoe of FIG. 18.
Figure 20:
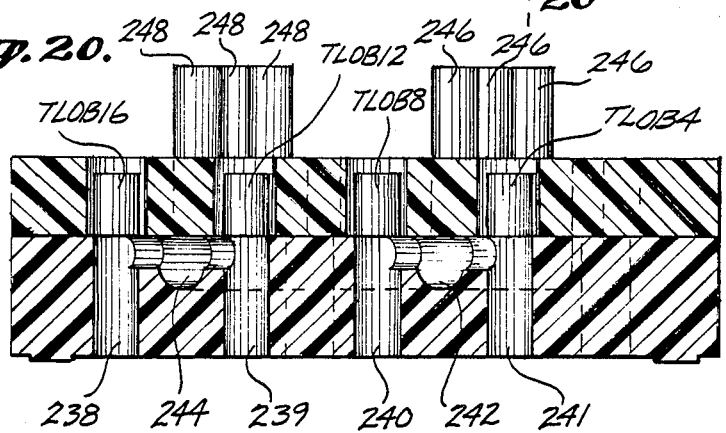
FIG. 20 is a cross-sectional view taken along line 20—20 of FIG. 19.

This horizontal placement, however, necessitates the use of reflectors to suitably direct the sound emitted and received by the loss-of-back transducers through an angle of 90 degrees. The arrangement and positioning of these reflectors are best seen in FIGS. 17A through 17C, which show loss-of-back transducers LOB6, LOB5, and LOB4 and their associated reflectors R6, R5, and R4. From these FIGS., and from FIG. 16, it will be seen that the reflectors are appropriately positioned vertically between the top and bottom surfaces of the main block 160 to correspond to the vertical placement of their associated transducers. The reflectors are also positioned in staggered relationship horizontally between the inner and outer surfaces of the main block so that each loss-of-back transducer inspects a specific portion of the lower flange, which portion is incrementally spaced by a predetermined amount from the web 34. The reflectors R1, R2, and R3 for the other three loss-of-back transducers LOB3, LOB2, and LOB1, respectively, are arranged with the same vertical positioning as reflectors R6, R5, and R4, respectively, but with a different horizontal positioning (see FIG. 16) so that they inspect more laterally outward portions of the lower flange 36.

Water for coupling transducers LOB4, LOB5, and LOB6 is supplied from a network of passages comprising an inlet channel 184 that connects with a common central channel 186, and individual delay channels 187, 188, and 189 for the transducers LOB4-6, respectively. As seen in FIGS. 17A through 17C, each of the delay channels is connected to the central channel 186 and extends from the face of its respective loss-of-back transducer to the associated reflector and then to an opening provided on the lower surface of the main block 160.

The water supply for the other three loss-of-back transducers LOB1-3 in the main block of the left lower flange shoe is substantially identical to that just described for transducers LOB4-6. Thus, water coupled into the block through an inlet channel 190 is fed through a central channel and delay channel that are substantially as shown in FIGS. 17A through 17C.

Referring again to FIGS. 15 and 16, the rearward end of the main block 160 carries the two transducers that inspect the lower radius 40 and the filler region between the web 34 and the lower flange 36. As shown in detail in FIGS. 17E and 17F, water for these transducers is fed into a central channel 192 by an inlet channel 194. From the central channel, the water is supplied through branch channels 195 and 196 to delay channels 198 and 200 that extend from the face of transducers L37.5R and LL45P, respectively, to openings provided on the lower inner corner of the main block 160, which corner is rounded for conformed, mating engagement with the lower radius of the I stiffener.

A fourth network of passageways is included in the front portion of the main block 160 to supply water for coupling the lower web transmit transducers WLT5-7. Referring to FIGS. 15 and 17D, this network comprises an inlet channel 202 that is connected to a central channel 204 and separate delay channels 206, 207, and 208 for transducers WLT5, WLT6, and WLT7, respectively. Each of these delay channels is connected to the central channel 204 and extends from its respective transducer to an opening on the inner face of the main block 160 that, in operation, is engaged with the side of the web 34 of the stiffener.

The main block 162 of the right lower flange shoe 50 has an arrangement of transducers, reflectors, and water passageways that mirrors the arrangement of transducers, reflectors, and passageways just described for the main block 160 of the left lower flange shoe 48. This can be clearly seen in FIG. 14, which is a right side isometric view that places the left lower flange shoe 48 in the background. For purposes of water distribution, the transducers are arranged in four groups and supplied via four inlet channels 210, 212, 214, and 216. In the rear of the block, inlet 210 feeds water into a connecting channel 218. From the connecting channel 218, water is supplied through branch channels 220 and 222 to the transducers RL45P and L37.5T that perform the inspection of the right lower radius 42 and the filler region between the web 34 and lower flange 36 of the stiffener. The transducer RL45P is oriented at an angle of 45 degrees to perform an angular pulse echo inspection of the radius region. This transducer includes a delay channel 224 that is arranged in identical manner to the delay channel 200 of the angular pulse echo transducer LL45P located in the opposite shoe 48, as shown in FIG. 17F. Similarly, transmit transducer L37.5T has a delay channel (not shown) that is identical to the delay channel 198 of its associated receive transducer L37.5R, as shown in FIG. 17E.

The central portion of the main block 162 contains the six loss-of-back transducers LOB7-12 and their associated reflectors R7 through R12 and water passages. The configuration of these elements will be readily understood from the previous discussion of the arrangement for the loss-of-back transducers LOB1-6 located in the opposite shoe. In addition, it will be recognized that the three lower web receive transducers WLR5-6 mounted in the rear of main block 162 have water passages configured in the manner described for their associated transmit transducers WLT5-7 located in the opposite shoe.

As previously discussed in conjunction with FIG. 3E, a separate toolside shoe 60 is used to provide additional inspection of the interface between the skin panel 38 and the lower flange 36 of the stiffener. As shown in FIG. 18, the toolside shoe 60 is mounted in a gimbal 230 so as to be pivotal about two orthogonal axes that extend between the sides of the shoe and intersect in the center. This gimballed arrangement enables the shoe to follow gradual changes in the contour of the surface being inspected. The gimbal-toolside shoe assembly is connected to a transport mechanism 236 through a pair of rods 232 and a mounting block 234. The rods 232 are slidably received by the mounting block 234 so that the gimbal and shoe assembly remain free to float vertically and thereby accommodate varying spacings between the transport mechanism 236 and the part under inspection.

The toolside shoe is a generally rectangular block having sixteen transducers TLOB1-16 that are arranged in a four-by-four matrix, wherein each transducer is equidistantly spaced from other adjacent transducers. Transducers TLOB1-16 are pulse echo transducers that are operated in a loss-of-back mode, i.e., the signals are gated on the back wall of the skin panel 38. Each of the transducers has a delay channel that extends from the face thereof to an opening on the undersurface of the shoe 60. The configurations of these delay channels are identical for each of the transducers and are as shown by the delay channels 238 through 241 in FIG. 20 for transducers TLOB16, TLOB12, TLOB8, and TLOB4. Each of the delay channels is connected to one or the other of two central channels 242 and 244. Water for coupling the transducers to the inspected part is supplied to the central channel 242 by three inlet tubes 246 and is supplied to the central channel 244 by three inlet tubes 248.

While a four-by-four matrix of transducers was used in the illustrated arrangement, it is to be understood that other matrix patterns or arrangements can be used, including patterns which are non-symmetrical.

Figure 21:
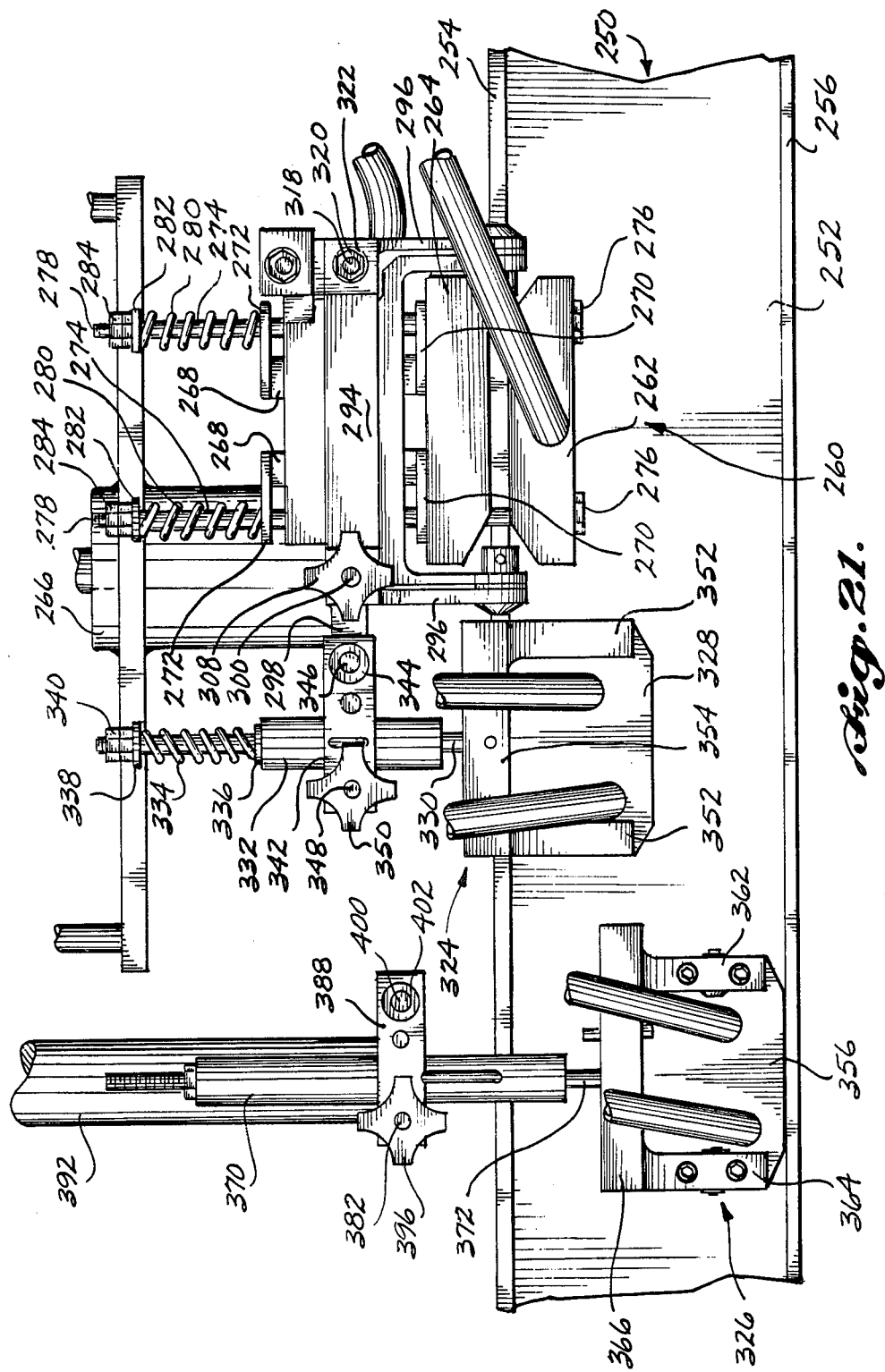
FIG. 21 is a side elevational view of an alternative embodiment of an ultrasonic inspection probe according to the invention.
Figure 22:
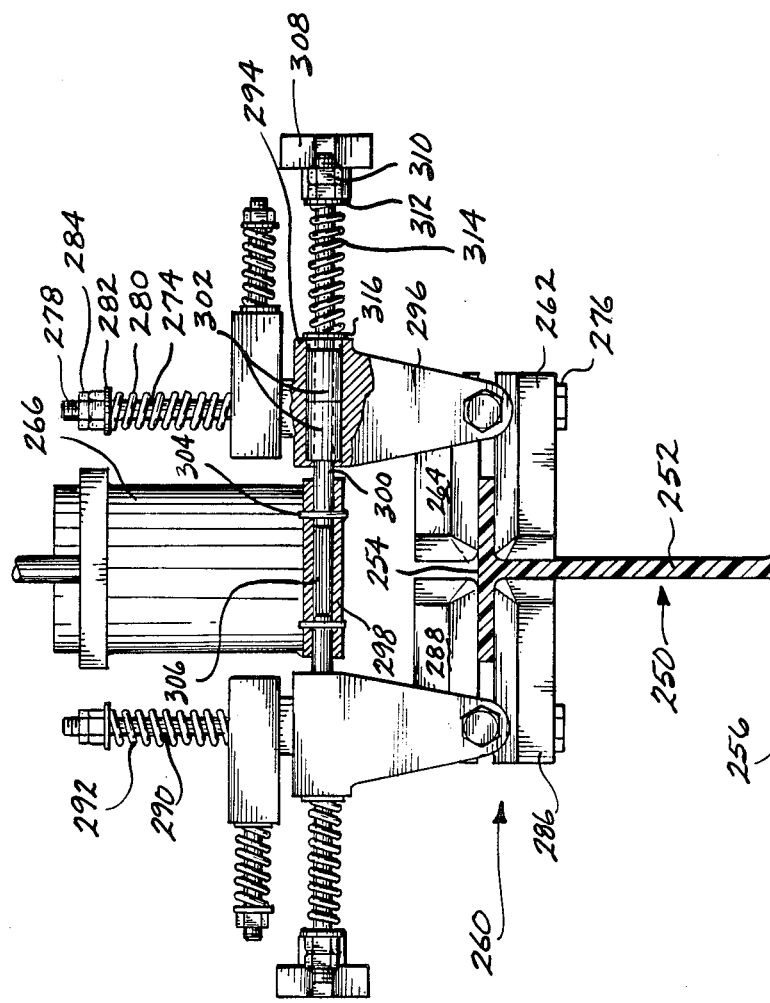
FIG. 22 is a rear elevational view, with parts broken, of the top flange shoe assembly of the probe of FIG. 21.
Figure 23:
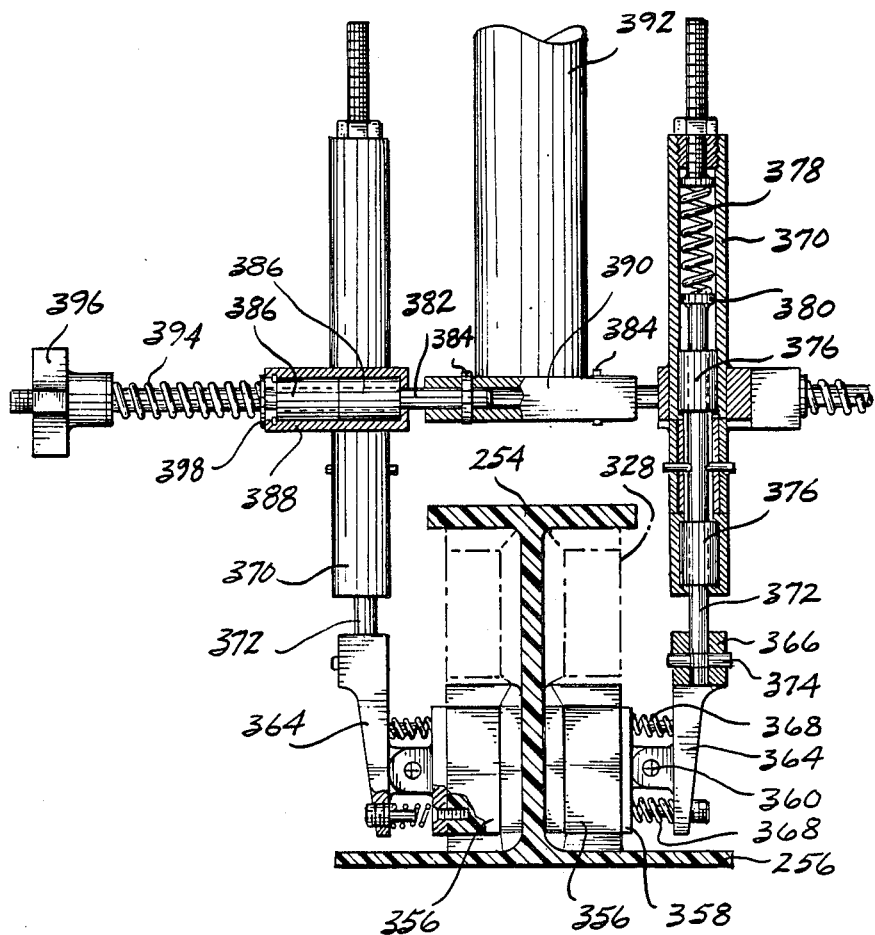
FIG. 23 is a rear elevational view, with parts broken, of the lower web shoe assembly of the probe of FIG. 21.

FIGS. 21 through 23 illustrate an alternative embodiment of an ultrasonic inspection probe formed in accordance with the invention. The probe has three separate shoe assemblies for inspecting different portions of the illustrated "I" structure 250. The constituent shoes of these assemblies have transducers and their associated water passages arranged to inspect the structures using the techniques previously discussed in conjunction with FIGS. 2 and 3A through 3C to locate and size flaws, particularly those occurring where the web intersects the top flange 254 and the bottom flange 256. The details of these transducers and passages have been omitted from FIGS. 21 through 23 to enable emphasis of the unique and important manner in which the shoes are interconnected to form the three assemblies and the probe. The details of the position and operation of the transducers will be readily appreciated from the previous discussion from which it will be recalled that: (a) a through-transmission technique is used to inspect the web and the flat portions of the top flange 254; (b) a radius-to-radius modified through-transmission technique is used to inspect the two lower radii; and (c) an angular in/normal out (double-sided radius inspection) techniques is used to inspect the upper radius regions.

Although no pulse echo transducers were used in this embodiment, it is to be appreciated that the probe holding/manipulating arrangement illustrated here can be used with shoes that have transducers for making pulse echo and/or pulse echo loss of back inspections.

The illustrated probe is designed to be held and manipulated by a gantry robot and, accordingly, is particularly well suited for use in a production mode. For this purpose, the shoe assemblies are arranged to have five degrees of freedom of movement, i.e., translational movement along three orthogonal axes and pivotal movement about two separate axes.

Referring now to FIGS. 21 and 22, a top flange shoe assembly 260 has four shoes that are connected in pairs to form separate left and right shoe halves. The shoes forming each half are interconnected by a spring-loaded mechanism that urges the shoes together for clamp-like engagement with the top flange of the I structure. As described below, two independent spring mechanisms are used to connect the halves to an arm 266, which is part of the probe holder that connects the probe to the gantry.

Considering now the details of the shoe halves, the right half has a right bottom shoe 262 and a right top shoe 264 configured for mating engagement with the undersurface and upper surface, respectively, of the top flange 254. A pair of generally U-shaped yokes 268 have lower legs 270 that are attached, for example, by screws, to the upper surface of the top shoe 264. An elongated pin 274 having a threaded end 278 and a hexagonal head 276 is fixed within the bottom shoe 262 and passes in succession through a bushing (not shown) in the top shoe 264 and the lower and upper legs 270 and 272 of each of the U-shaped yokes 268. The bushings for the two pins permit sliding, translational movement of the top shoe relative to the bottom shoe. The assembly of the top shoe and the two yokes is restrained in its movement and normally urged toward the bottom shoe 262 by a pair of springs 280. Each spring is held in a state of compression between the upper leg 272 of its respective yoke 268 and a washer 282 that is held on the threaded end of the pin 274 by a nut 284. With this arrangement, it will be seen that the spring forces transferred through the yokes 268 to the top shoe 264 draw the two shoes together into tight engagement with the top flange of the I structure.

An identical arrangement is used to spring load the left top shoe 288 toward the left bottom shoe 286 to clamp the opposite side of the top flange 254. The construction and arrangement of this mechanism will be readily understood from the preceding discussion and from FIG. 22, which shows the elongated pin 290 and compression spring 292 for the left half shoe assembly.

In the first embodiment of the probe discussed above, the upper flange/web shoe assembly includes springs that urge the constituent shoes together in two directions so that the assembly is self-supporting when attached to the upper flange of an I structure. In the alternative embodiment of FIGS. 21 through 23 now under discussion, the shoe assembly is relieved of the burden of holding itself together and to the part in two directions. While the assembly retains the responsibility of holding the shoes in the vertical direction as seen in the FIGS., the function of holding the shoes together in the horizontal direction of the FIGS. is transferred to the probe holder mechanism.

This spring-loaded holding mechanism is identical for the left and right halves of the probe. This mechanism includes a frame 294 having opposed arms 296 that extend downwardly over the front and rear sides of the top and bottom shoes. Although not shown in the FIGS. the frame includes bushings through which the pins 274 pass and thereby slidably mount the right half assembly of shoes and yokes to the frame. This resultant assembly is, in turn, mounted upon an elongated platform 298 that is connected to the bottom of the arm 266 of the probe holder. As seen best in FIG. 22, the upper rear portion of the frame 294 has a pair of bushings 302 that slidably receive a rod 300. One end of the rod 300 is fixed by an expansion pin 304 in a bore 306 that is formed n the platform 298. The opposite end of the rod is threaded and has mounted thereon a knob 308, a nut 310, and a washer 312. A spring 314 is held in a state of compression between washer 312 and another washer 316 that bears against the side of the frame 294.

Although not shown in the drawings, a substantially identical arrangement is used to connect the opposite end of the frame to the platform of the probe holder. This mechanism includes a rod 318 (see FIG. 21) that is fixed in a bore formed in the platform 298 and that is received by bushings provided in the frame 294. A nut 320 and washer 322 are attached to a threaded end of the rod 318 and serve to compress a spring against a washer in the same manner that the nut 310 and washer 312 compress the spring 314 against the washer 316 at the opposite end of the frame. Consequently, it will be appreciated that the mounting arrangement at the front end of the frame is the same as the mounting arrangement used at the rear end of the frame, with the exception of the omission of a knob corresponding to knob 308.

As a result of this arrangement, the entire right half assembly is mounted for limited translational movement along the rods 300 and 318 against the force of the springs. The compression of the springs is adjusted so that the bottom shoe 262 is normally forced into conforming engagement with the upper portion of the web 252. The tensioning of the other two compression springs 280 is also suitably adjusted to ensure that the top and bottom shoes are normally maintained in conforming engagement with the flange 254. Importantly, the combined forces of the springs push the rounded edge of the bottom shoe 262 into mating engagement with the critical radius region. Since the shoes float against the forces of the springs on the rods 300 and 318 and the pins 274, the shoes maintain this conformed engagement while they are transported along the part.

To inspect the remainder of the I structure, the probe includes an upper web shoe assembly 324 and a lower web shoe assembly 326 that are independently mounted to the probe holder. Each of these assemblies comprises a pair of identical shoes and associated mounting mechanism that are arranged symmetrically on opposite sides of the probe holder so their aligned pairs of transmit and receive transducers may be moved to cooperatively perform through-transmission inspection of the web 252 and, in the case of the lower assembly, radius-to-radius through transmission inspection of the lower flange. Considering the upper web shoe assembly 324 first, this assembly has an upper web shoe 328 that is mounted for limited translational movement by means of a rod 330 and bushings (not shown) that are contained within a cylinder 332. A spring 334 is maintained in a state of compression between washers 336 and 338 that bear, respectively, against the cylinder 332 and a nut 340 that is received on a threaded end of the rod 330. In operation, the force of the spring draws the upper web shoe 328 into engagement with the undersurface of the top flange 254 (see FIG. 23). The cylinder 332 is secured to a block 342 that, in turn, is mounted to the platform 298 of the probe holder for limited translational movement. At the front of the block, this attachment is by means of a bushing 344 and a rod that is connected to the platform 298 and slidingly received by the bushing. The rear of the block contains two bushings through which a rod 348 passes. The inner end of the rod is affixed in a bore provided in the platform 298, while the other end is threaded to receive a knob 350. A spring (not shown), identical to spring 394 is maintained in compression between the knob 350 and the block 342 in a manner similar to that described above in conjunction with the knob 308 and spring 314, which biases the top flange shoe assembly toward the I structure. The spring just described that is compressed between the block 342 and knob 350 functions to bias the upper web shoe assembly in a similar manner. Additional biasing of the upper web shoe 328 toward the web of the I structure is provided by means of four springs that are not shown, but that will be understood by the discussion that follows of the springs that bias the lower web shoe assemblies against the part under inspection. Briefly, these springs extend between the upper web shoe 328 and two arms 352 of the frame 354 that mounts the upper web shoe to the rod 330.

As shown in detail in FIG. 23, the lower web shoe assembly 326 consists of two symmetrical structures that function to position a pair of lower web shoes 356 on opposite sides of the I-structure and in conformed, mating engagement with the lower portions of the web, the lower flange, and the radius areas in between. A plate 358 is attached to the outer face of the lower web shoe and pivotally connected by means of a pin 360 to front and rear arms of a mounting frame 366. A pair of springs 368 extend between each of the arms 362 and 364 and the plate 358 that is attached to the lower web shoe to provide resiliency that maintains the desired engagement between the shoe and the part under inspection. The assembly consisting of the mounting frame 366 and the lower web shoe 356 is mounted for limited translational movement in a cylinder 370. As shown in FIG. 23, this mounting is by means of a rod 372 that has one end affixed to the frame by means of a pin 374. The rod is slidingly received by a pair of bushings 376 that are mounted within the cylinder. A spring 378 contained within the cylinder bears against a disc-shaped end 380 and functions in operation to urge the lower web shoe 356 into engagement with the flange 256. A spring and rod arrangement similar to those described above for the other web shoe assemblies urges the shoes of the lower web shoe assembly laterally into engagement with the sides of the web. This arrangement includes a rod 382 that has one end attached by a pin 384 to the lower end 390 of an auxiliary arm 392 of the probe holder. A spring 394 is maintained in a compressed state between a knob 396 and a washer 398 that bears against the block 388. In a manner similar to the arrangements previously described, this spring urges the entire half of the lower web shoe assembly inwardly and into engagement with the I structure. For this purpose, the structure slides along the rod 382 and along a shorter rod that has one end attached to the lower end 390 of the auxiliary arm and the other arm received in a bushing 402.

While preferred embodiments have been illustrated and described, it will be appreciated that various changes can be made therein without departing from the spirit and scope of the invention. For example, as briefly noted above, the shoes and transducers mounted therein can be arranged to inspect composite parts that intersect at angles other than 90 degrees. In addition, the transducers may be arranged in a wide variety of patterns and angles to inspect in different patterns and in different directions than have been illustrated. For example, the transmit and receive transducers used to inspect the upper flange 32 can be reversed so that the inspection of this portion of the structure is made in a direction from the bottom to the top rather than from the top to the bottom as illustrated in FIGS. 3A and 3B. In such an embodiment, the radius area would be inspected by a sound that is injected into each of the radii 44 and 46 and travels through the filler area and out of the top of the upper flange 32 where it would be received by a transducer of transducers mounted in the top shoes. It will be appreciated that other changes can be made without departing from the spirit and the scope of this invention. Consequently, it will be recognized that the invention can be practiced otherwise than as specifically described herein.

The embodiments of the invention in which an exclusive property or privilege is claimed are defined as follows:

1. An ultrasonic inspection probe for determining the presence, location, and size of flaws in the radius region formed between two intersecting elements of a laminated structure, said probe comprising:
   a pair of shoes, said shoes being configured for complementary mating engagement with opposite sides of the radius region of said laminated structure; and
   a plurality of ultrasonic transducers mounted on each of said shoes so as to be oriented in predetermined relationships to said structure when said shoes are engaged therewith, said plurality of transducers including:
   at least one pulse echo transducer oriented to direct ultrasonic signals in a predetermined angular direction into the radius region of said structure, said pulse echo transducer being operable in a pulse echo mode to receive reflections of said ultrasonic signals;
   at least one transmit transducer mounted in one of said shoes and oriented to direct ultrasonic signals in a predetermined angular direction into said radius region; and
   at least one receive transducer mounted in the other one of said shoes on the opposite side of said radius region, said receive transducer being oriented in a predetermined angular relationship to said transmit transducer and to said radius region to receive ultrasonic signals transmitted into the radius region by said transmit transducer.

2. The probe of claim 1, wherein said plurality of transducers includes a second pulse echo transducer mounted in the other one of said shoes so as to be positionable on the opposite side of said radius region, said second pulse echo transducer being oriented to direct ultrasonic signals in a predetermined angular direction into the radius region of said structure, said second pulse echo transducer being operable in a pulse echo mode to receive reflections of the ultrasonic signals transmitted thereby.

3. The probe of claim 2, wherein said pulse echo transducers are oriented in their respective shoes to transmit and receive ultrasonic signals along paths that are at equal but opposite angles relative to said radius region.

4. The probe of claim 3, wherein said transmit transducer and said receive transducer are oriented in their shoes to respectively transmit and receive ultrasonic signals along paths that are at equal but opposite angles relative to said radius region.

5. The probe of claim 2, wherein said radius region comprises the radius region of two elements that intersect to form a T-shaped cross section, and wherein each of said pulse echo transducers is oriented to transmit and receive ultrasonic signals along a path that is at an angle of about 45 degrees relative to said radius region.

6. The probe of claim 5, wherein said transmit transducer and said receive transducer are oriented in their respective shoes to transmit and receive ultrasonic signals along a path that is at an angle of about 37.5 degrees relative to said radius region.

7. The probe of claim 2, wherein said plurality of transducers includes transducers for inspecting portions of said structure adjacent said radius region.

8. An ultrasonic inspection probe for determining the presence, location, and size of flaws in a laminated structure of a type having a web and flange that intersect at substantially right angles, said structure having a radius region where said web and flange intersect, the exterior surfaces of said web and flange defining a first corner in said radius region, said probe comprising:
   transducer mounting means;
   a radius-to-radius transmit transducer mounted on said transducer mounting means, said radius-to-radius transmit transducer being positionable adjacent said first corner oriented to transmit ultrasonic signals into the radius region of said laminated structure in a direction that forms a predetermined angle relative to a reference plane that contains the side of said flange that defines said first corner;
   a radius-to-radius receive transducer mounted on said transducer mounting means so as to be positionable on the side of said web that is opposite said first corner, said radius-to-radius receive transducer being oriented in a direction that forms a predetermined angle relative to said reference plane to receive ultrasonic signals transmitted by said radius-to-radius transmit transducer;
   a radius-to-flange transmit transducer mounted on said transducer mounting means so as to be positionable adjacent the side of said flange that lies opposite said first corner and in predetermined alignment with said web, said radius-to-flange transmit transducer being oriented to transmit ultrasonic signals into said radius region in a direction that forms a predetermined angle relative to said reference plane; and
   a radius-to-flange receive transducer mounted on said transducer mounting means so as to be positionable adjacent said first corner and oriented in a direction that forms a predetermined angle relative to said reference plane to receive ultrasonic signals transmitted by said radius-to-flange transmit transducer.

9. The probe of claim 8, wherein:
   said radius-to-flange transmit transducer is oriented substantially perpendicular to said reference plane and in alignment with a plane that contains the side of said web that forms first corner; and
   said radius-to-flange receive transducer is oriented at an angle of about 45 degrees relative to said reference plane.

10. The probe of claim 9, wherein said radius-to-radius transmit transducer and said radius-to-radius receive transducer are each oriented at an angle of about 37.5 degrees relative to said reference plane.

11. The probe of claim 8, further including:
   a through-flange transmit transducer mounted on said transducer mounting means so as to be positionable adjacent the side of said flange that lies opposite said first corner and oriented to transmit ultrasonic signals into a portion of said flange that is spaced apart from said first corner and adjacent said radius region;
   a through-flange receive transducer mounted on said transducer mounting means so as to be positionable adjacent said first corner, said through-flange receive transducer being alignable with said through-flange transmit transducer to receive the ultrasonic signals transmitted thereby;
   a through-web transmit transducer mounted on said transducer mounting means so as to be positionable adjacent said first corner and oriented to transmit ultrasonic signals into a portion of the web that is spaced apart from said first corner and said radius region; and a through-web receive transducer mounted on said transducer mounting means so as to be positionable adjacent the side of said web that lies opposite said first corner, said through-web receive transducer being alignable with said through-web transmit transducer to receive the ultrasonic signals transmitted thereby.

12. The probe of claim 11, further including:

a plurality of through-flange transmit transducers mounted at spaced-apart positions on said transducer mounting means so that each of said through-flange transmit transducers is positionable adjacent the side of said flange that lies opposite said first corner and in predetermined spaced-apart relation to each other such transducer, said through-flange transmit transducers being oriented to transmit ultrasonic signals into said flange;

a plurality of through-flange receive transducers for receiving the ultrasonic signals transmitted by said plurality of through-flange transmit transducers, said through-flange receive transducers being mounted on said transducer mounting means so as to be positionable in predetermined spaced-apart relation to said first corner, said through-flange receive transducers being located at spaced-apart positions that correspond to the spaced-apart positions of said through-flange transmit transducers so that each of said through-flange receive transducers is alignable with a selected one of said through-flange transmit transducers;

a plurality of through-web transmit transducers mounted at spaced-apart positions on said transducer mounting means so that each of said through-web transmit transducers is positionable in predetermined spaced-apart relation to said first corner, said through-web transmit transducers being oriented to transmit ultrasonic signals into said web; and a plurality of through-web receive transducers to receive the ultrasonic signals transmitted by said plurality of through-web transmit transducers, said through-web receive transducers being mounted on said transducer mounting means so as to be positionable adjacent the side of said web that lies opposite said first corner, said through-web receive transducers being located at spaced-apart positions that correspond to the spaced-apart positions of said through-web transmit transducers so that each of said through-web receive transducers is alignable with a selected one of said through-web transmit transducers.

13. The probe of claim 8, wherein said web and flange intersect to form a T-shaped cross section, said web and flange forming a second corner opposite said first corner, and wherein said radius-to-radius receive transducer is positionable adjacent said second corner and further including:

a second radius-to-flange transmit transducer mounted on said transducer mounting means so as to be positionable adjacent the side of said flange that lies opposite said second corner and in predetermined alignment with said web, said second radius-to-flange transmit transducer being oriented to transmit ultrasonic signals into said radius region in a direction that forms a predetermined angle relative to said reference plane; and a second radius-to-flange receive transducer mounted on said transducer mounting means and oriented so as to be positionable adjacent said second corner in a direction that forms a predetermined angle relative to said reference plane to receive ultrasonic signals transmitted by said second radius-to-flange transmit transducer.

14. The probe of claim 13, wherein:

said second radius-to-flange transmit transducer is oriented so as to be positionable substantially perpendicular to said reference plane and in alignment with a plane that contains the side of said web that forms said second corner, and said second radius-to-flange receive transducer is oriented at an angle of about 45 degrees relative to said reference plane.

15. The probe of claim 13, further including:

a through-flange transmit transducer mounted on said transducer mounting means so as to be positionable adjacent the side of said flange that lies opposite said first corner and oriented to transmit ultrasonic signals into a portion of said flange that is spaced apart from said first corner and said radius region;

a through-flange receive transducer mounted on said transducer mounting means so as to be positionable adjacent said first corner, said through-flange receive transducer being alignable with said through-flange transmit transducer to receive the ultrasonic signals transmitted thereby;

a through-web transmit transducer mounted on said transducer mounting means so as to be positionable adjacent said first corner and oriented to transmit ultrasonic signals into a portion of said web that is spaced apart from said first corner and said radius region; and a through-web receive transducer mounted on said transducer mounting means and positioned so as to be adjacent the side of said web that lies opposite said first corner, said through-web receive transducer being alignable with said through-web transmit transducer to receive the ultrasonic signals transmitted thereby.

16. The probe of claim 15, further including:

a plurality of through-flange transmit transducers mounted at spaced-apart positions on said transducer mounting means so that selected ones of said through-flange transmit transducers are positionable adjacent the side of said flange that lies opposite said first corner and in predetermined spaced-apart relation to each other, each of said through-flange transmit transducers being oriented to transmit ultrasonic signals into said flange;

a plurality of through-flange receive transducers for receiving the ultrasonic signals transmitted by said plurality of through-flange transmit transducers, said through-flange receive transducers being mounted on said transducer mounting means in predetermined spaced-apart relation to one of said corners and at spaced-apart positions that correspond to the spaced-apart positions of said through-flange transmit transducers so that each of said through-flange receive transducers is alignable with a selected one of said through-flange transmit transducers;

a plurality of through-web transmit transducers mounted at spaced-apart positions on said transducer mounting means so that said through-web transmit transducers are positionable in predetermined spaced-apart relation to said first corner and oriented to transmit ultrasonic signals into said web; and a plurality of through-web receive transducers for receiving the ultrasonic signals transmitted by said plurality of through-web transmit transducers, said through-web receive transducers being mounted on said transducer mounting means adjacent the side of said web that lies opposite said first corner and at spaced-apart positions that correspond to the spaced-apart positions of said through-web transmit transducers so that each of said through-web receive transducers is alignable with a selected one of said through-web transmit transducers.

17. The probe of claim 8, further, including:

a through-web transmit transducer mounted on said transducer mounting means so as to be positionable adjacent said first corner and oriented to transmit ultrasonic signals into a portion of said web that is spaced apart from said first corner and said radius region;

a through-web receive transducer mounted on said transducer mounting means so as to be positionable adjacent the side of said web that lies opposite said first corner, said through-web receive transducer being alignable with said through-web transmit transducer to receive the ultrasonic signals transmitted thereby; and a loss-of-back transducer mounted on said transducer mounting means so as to be positionable adjacent said first corner and oriented to transmit ultrasonic signals into a portion of said flange that is spaced apart from said first corner and said radius region, said loss-of-back transducer being operable in a loss-of-back mode to receive reflections of the ultrasonic signals transmitted thereby.

18. The probe of claim 17, further including:

a plurality of through-web transmit transducers mounted at spaced-apart positions on said transducer mounting means so as to be positionable in predetermined spaced-apart relation to said first corner, each of said through-web transmit transducers being oriented to transmit ultrasonic signals into said web;

a plurality of through-web receive transducers for receiving the ultrasonic signals transmitted by said plurality of through-web transmit transducers, said through-web receive transducers being mounted on said transducer mounting means so as to be positionable adjacent the side of said web that lies opposite said first corner, said through-web receive transducers being located at spaced-apart positions that correspond to the spaced-apart positions of said through-web transmit transducers so that each of said through-web receive transducers is alignable with a selected one of said through-web transmit transducers; and a plurality of loss-of-back transducers mounted at spaced-apart positions on said transducer mounting means so as to be positionable in predetermined spaced-apart relation to said first corner and oriented to transmit ultrasonic signals into spaced-apart portions of said flange, each of said loss-of-back transducers being operable in a loss-of-back mode to receive reflections of its respectively transmitted ultrasonic signals.

19. The probe of claim 13, further including:

a plurality of loss-of-back transducers mounted on said transducer mounting means and oriented to transmit ultrasonic signals into said flange, at least one of said loss-of-back transducers being mounted so as to be positionable adjacent said first corner and at least one of said loss-of-back transducers being mounted so as to be positionable adjacent said second corner, each of said loss-of-back transducers being operable in a loss-of-back mode to receive reflections of its respectively transmitted ultrasonic signals.

20. The probe of claim 19, further including:

a through-web transmit transducer mounted on said transducer mounting means so as to be positionable adjacent said first corner and oriented to transmit ultrasonic signals into a portion of said web that is spaced apart from said first corner and said radius region; and a through-web receive transducer mounted on said mounting means so as to be positionable adjacent said second corner, said through-web receive transducer being alignable with said through-web transmit transducer to receive the ultrasonic signals transmitted thereby.

21. The probe of claim 20, further including:

a plurality of through-web transmit transducer mounted at spaced-apart positions on said transducer mounting means so that said through-web transmit transducers are positionable in predetermined spaced-apart relation to said first corner and oriented to transmit ultrasonic signals into said web;

a plurality of through-web receive transducers for receiving the ultrasonic signals transmitted by said plurality of through-web transmit transducers, said through-web receive transducers being mounted on said transducer mounting means adjacent the side of said web that lies opposite said first corner and at spaced-apart positions that correspond to the spaced-apart positions of said through-web transmit transducers so that each of said through-web receive transducers is alignable with a selected one of said through-web transmit transducers; and a plurality of loss-of-back transducers mounted at spaced-apart positions on said transducer mounting means so as to be positionable in predetermined spaced-apart relation to said first corner, said loss-of-back transducers being oriented to transmit ultrasonic signals into said flange, each of said loss-of-back transducers being operable in a loss-of-back mode to receive reflections of the ultrasonic signals transmitted thereby.

22. An ultrasonic inspection probe for determining the presence, location, and the size of flaws in a laminated structure of a type having a web and flange that intersect at substantially right angles, said structure having a radius region where said web and flange intersect, the exterior surfaces of said web and flange defining a first corner in said radius region, said probe comprising:

transducer mounting means;

a radius-to-radius transmit transducer mounted on said transducer mounting means, said radius-to-radius transmit transducer being positionable adjacent said first corner and oriented to transmit ultrasonic signals into the radius region of said laminated structure in a direction that forms a predetermined angle relative to a reference plane that contains the side of said flange that defines said first corner;

a radius-to-radius receive transducer mounted on said transducer mounting means so as to be positionable on the side of said web that is opposite said first corner, said radius-to-radius receive transducer being oriented in a direction that forms a predetermined angle relative to said reference plane to receive ultrasonic signals transmitted by said radius-to-radius transmit transducer;

a radius-to-flange transmit transducer mounted on said transducer mounting means so as to be positionable adjacent said first corner and oriented to transmit ultrasonic signals into said radius region in a direction that forms a predetermined angle relative to said reference plane;

a radius-to-flange receive transducer mounted on said transducer mounting means so as to be positionable adjacent the side of said flange that lies opposite said first corner and in predetermined alignment with said web, said radius-to-flange receive transducer being oriented to receive ultrasonic signals transmitted by said radius-to-flange receive transducer.

23. The probe of claim 22 wherein:

said radius-to flange receive transducer is oriented substantially perpendicular to said reference plane and in alignment with the plane that contains the side of said web that forms said first corner;

said radius-to-flange transmit transducer is oriented at an angle of about 45 degrees relative to said reference plane; and said radius-to-radius transmit transducer and said radius-to-radius receive transducer are each oriented at an angle of about 37.5 degrees relative to said reference plane.

24. An ultrasonic inspection probe for determining the presence, location, and size of flaws in an I-shaped laminated structure, said structure having a web, an upper flange, and a lower flange, said flanges intersecting said web at substantially right angles to define upper and lower radius regions, left and right upper corners, and left and right lower corners, said probe comprising:

a left upper pulse echo transducer positionable adjacent said left upper corner and oriented to transmit ultrasonic signals into said upper radius region at a predetermined angle relative to an upper reference plane that contains the side of said flange that forms said left upper corner;

a right upper pulse echo transducer positionable adjacent said right upper corner and oriented to transmit ultrasonic signals into said upper radius region at a predetermined angle relative to said upper reference plane;

an upper radius-to-radius transmit transducer positionable adjacent said left upper corner and oriented to transmit ultrasonic signals into said upper radius region in a direction that forms a predetermined angle relative to said upper reference plane;

an upper radius-to-radius receive transducer positionable adjacent said right upper corner and oriented in a direction that forms a predetermined angle relative to said upper reference plane to receive ultrasonic signals transmitted by said radius-to-radius transmit transducers;

a left lower pulse echo transducer positionable adjacent said left lower corner and oriented to transmit ultrasonic signals into said lower radius region at a predetermined angle relative to a lower reference plane that contains the side of said flange that forms said left lower corner;

a right lower pulse echo transducer positionable adjacent said right lower corner and oriented to transmit ultrasonic signals into said lower radius region at a predetermined angle relative to said lower reference plane;

a lower radius-to-radius transmit transducer positionable adjacent said left lower corner and oriented to transmit ultrasonic signals into said lower radius region in a direction that forms a predetermined angle relative to said lower reference plane;

a lower radius-to-radius receive transducer positionable adjacent said right lower corner and oriented in a direction that forms a predetermined angle relative to said lower reference plane to receive ultrasonic signals transmitted by said lower radius-to-radius transmit transducers and;

mounting means for supporting said transducers in their respective orientations.

25. The probe of claim 24, further including:

a plurality of loss-of-back transducers mounted at spaced-apart positions on said mounting means so as to be positionable in predetermined spaced-apart relation to said lower radius region and oriented so as to transmit ultrasonic signals into said lower flange, at least one of said loss-of-back transducers being positionable in spaced-apart relation to said left lower corner and at least one of said loss-of-back transducers being positionable in spaced-apart relation to said right lower corner, each of said loss-of-back transducers being operable in a loss-of-back mode to receive reflections of the ultrasonic signals transmitted thereby.

26. The probe of claim 24, further including:

a left upper flange transmit transducer mounted on said mounting means so as to be positionable adjacent the side of said upper flange that lies opposite said left upper corner, said left upper flange transmit transducer being oriented to transmit ultrasonic signals into a portion of said upper flange that is adjacent said upper radius region;

a left upper flange receive transducer mounted on said mounting means so as to be positionable in adjacent, spaced-apart relation to said left upper corner, said left upper flange receive transducer being alignable with said left upper flange transmit transducer to receive the ultrasonic signals transmitted thereby;

an upper web transmit transducer mounted on said mounting means so as to be positionable in adjacent, spaced-apart relation to said left upper corner, said upper web transmit transducer being oriented to transmit ultrasonic signals into a portion of said web that is adjacent said upper radius region; and an upper web receive transducer mounted on said mounting means so as to be positionable in adjacent, spaced-apart relation to said right upper corner and in alignment with said upper web transmit transducer to receive the ultrasonic signals transmitted thereby.

27. The probe of claim 26, further including:

a lower web transmit transducer mounted on said mounting means so as to be positionable in adjacent, spaced-apart relation to said left lower corner, said lower web transmit transducer being oriented to transmit ultrasonic signals into a portion of aid web that is adjacent said lower radius region; and a lower web receive transducer mounted on said mounting means so as to be positionable in adjacent, spaced-apart relation to said right lower corner and in alignment with said lower web transmit transducer to receive the ultrasonic signals transmitted thereby.

28. An ultrasonic inspection probe for determining the presence, location, and size of flaws in an elongate laminated structure having an I-shaped cross section, said structure having a web, an upper flange, and a lower flange, said flanges intersecting said web at substantially right angles to define upper and lower radius regions, left and right upper corners, and left and right lower corners, said probe comprising:
  (a) a right top shoe configured for mating engagement with portions of the side of said upper flange that lies opposite said upper corners, said right top shoe including:
    (i) a right upper radius transmit transducer mounted so as to be positionable adjacent a right portion of the side of said upper flange that lies opposite said right upper corner, said right upper radius transmit transducer being oriented to transmit ultrasonic signals into said upper radius region in a direction that forms a predetermined angle relative to an upper reference plane that contains the side of the upper flange that forms said left upper corner; and
    (ii) a right upper flange transmit transducer mounted so as to be positionable adjacent the side of said flange that lies opposite said right upper corner, said right upper flange transmit transducer being oriented to transmit ultrasonic signals into said right portion of the upper flange;
  (b) a left top shoe configured for mating engagement with portions of the side of said upper flange that lie opposite said upper corners, said left top shoe including:
    (i) a left upper flange transmit transducer mounted so as to be positionable adjacent a left portion of the side of said flange that lies opposite said left upper corner, said left upper flange transmit transducer being oriented to transmit ultrasonic signals into said left portion of the upper flange;
  (c) a left upper flange shoe configured for complementary mating engagement with a left portion of said upper flange, with a left upper portion of said web, and with said left upper corner, said left upper flange shoe and said left top shoe being resiliently biased toward one another, said left upper flange shoe including:
    (i) a left upper flange receive transducer mounted so as to be positionable in adjacent, spaced-apart relation to said left upper corner, said left upper flange receive transducer being alignable with said left upper flange transmit transducer to receive the ultrasonic signals transmitted thereby;
    (ii) an upper web transmit transducer mounted so as to be positionable in adjacent, spaced-apart relation to said left upper corner, said upper web transmit transducer being oriented to transmit ultrasonic signals into said upper portion of the web; and
    (iii) a first upper radius-to-radius transmit transducer mounted adjacent said left upper corner and oriented to transmit ultrasonic signals into said upper radius region at a predetermined angle relative to said upper reference plane;
  (d) a right upper flange shoe configured for complementary mating engagement with a right portion of said upper flange, with a right upper portion of said web, and with said right upper corner, said right upper flange shoe and said right top shoe being resiliently biased toward one another, said right upper flange shoe including:
    (i) a right upper flange receive transducer mounted so as to be positionable in adjacent, spaced-apart relation to said right upper corner, said right upper flange receive transducer being alignable with said right upper flange transmit transducer to receive the ultrasonic signals transmitted thereby;
    (ii) an upper web receive transducer mounted so as to be positionable in adjacent, spaced-apart relation to said right upper corner and in alignment with said upper web transmit transducer to receive the ultrasonic signals transmitted thereby;
    (iii) a first upper radius-to-radius receive transducer mounted adjacent said right upper corner and oriented in a direction that forms a predetermined angle relative to said upper reference plane to receive ultrasonic signals transmitted by said first upper radius-to-radius transmit transducer; and
    (iv) a right upper radius receive transducer mounted so as to be positionable adjacent said right upper corner and oriented at a predetermined angle relative to said upper reference plane to receive ultrasonic signals transmitted by the right upper radius transmit transducer that is mounted in said right to shoe.

29. The probe of claim 28, wherein: said right top shoe includes:
  a plurality of right upper flange transmit transducers mounted at spaced-apart positions so that each of said right upper flange transmit transducers is positionable adjacent the side of said flange that lies opposite said right upper corner and in predetermined spaced apart relation to each other such transducer, said right upper flange transmit transducers being oriented to transmit ultrasonic signals into said upper flange;
said left top shoe includes:
  a plurality of left upper flange transmit transducers mounted at spaced-apart positions such that each of said left upper flange transmit transducers is positionable adjacent the side of said flange that lies opposite said left upper corner and in predetermined spaced-apart relation to each other such transducer, said left upper flange transmit transducers being oriented to transmit ultrasonic signals into said upper flange;
said left upper flange shoe includes:
  a plurality of upper web transmit transducers mounted at spaced-apart positions so that each of said upper web transmit transducers is positionable in predetermined spaced relation to said left upper corner, said upper web transmit transducers being oriented to transmit ultrasonic signals into said web;

a plurality of left upper flange receive transducers for receiving the ultrasonic signals transmitted by said plurality of left upper flange transmit transducers, said left upper flange receive transducers being mounted at spaced-apart positions that correspond to the spaced-apart positions of said left upper flange transmit transducers so that each of said left upper flange receive transducers is alignable with a selected one of said left upper flange transmit transducers;

said right upper flange shoe includes:
a plurality of upper web receive transducers for receiving the ultrasonic signals transmitted by said plurality of upper web transmit transducers, said upper web receive transducers being mounted at spaced-apart positions that correspond to the spaced-apart positions of said upper web transmit transducers so that each of said upper web receive transducers is alignable with a selected one of said upper web transmit transducers; and
a plurality of right upper flange receive transducers for receiving the ultrasonic signals transmitted by said plurality of right upper flange transmit transducers, said right upper flange receive transducers being mounted at spaced-apart positions that correspond to the spaced-apart positions of said right upper flange transmit transducers so that each of said right upper flange receive transducers is alignable with a selected one of said right upper flange transmit transducers.

30. The probe of claim 29, wherein:
said left top shoe includes a left upper radius transmit transducer mounted so as to be positionable adjacent the portions of the side of said flange that lie opposite said upper corners to transmit ultrasonic signals into said upper radius region, said left upper radius transmit transducer being oriented in a direction that forms a predetermined angle relative to said upper reference plane; and
said left upper flange shoe includes a left upper radius receive transducer mounted so as to be positionable adjacent said left upper corner and oriented to receive ultrasonic signals transmitted by said left upper radius transmit transducer, said left upper radius receive transducer being oriented in a direction that forms a predetermined angle relative to said upper reference plane.

31. The probe of claim 30, wherein said right upper flange shoe and said left upper flange shoe are resiliently biased toward one another so as to clamp said laminated structure therebetween.

32. The probe of claim 29, further including:
a right lower shoe configured for complementary mating engagement with said lower flange, with a lower portion of said web, and with said right lower corner, said right lower shoe including:
a lower radius-to-radius transmit transducer mounted adjacent said right lower corner and oriented to transmit ultrasonic signals into said lower radius region at a predetermined angle relative to a lower reference plane that contains the side of the flange that forms said right lower corner;
a right lower pulse echo transducer positionable adjacent said right lower corner and oriented to transmit ultrasonic signals into said lower radius region at a predetermined angle relative to said lower reference plane;
a left lower shoe configured for complementary mating engagement with said lower flange, with a lower portion of said web, and with said left lower corner, said left lower shoe including:
a left lower pulse echo transducer positionable adjacent said left lower corner and oriented to transmit ultrasonic signals into said lower radius region at a predetermined angle relative to said lower reference plane; and
a lower radius-to-radius receive transducer positioned adjacent said left lower corner and oriented in a direction that forms a predetermined angle relative to said lower reference plane to receive ultrasonic signals transmitted by said lower radius-to-radius transmit transducer.

33. The probe of claim 32, wherein:
said left lower shoe further includes:
a lower web transmit transducer mounted so as to be positionable in adjacent, spaced-apart relation to said left lower corner, said lower web transmit transducer being oriented to transmit ultrasonic signals into said lower portion of the web; and
a left loss-of-back transducer mounted so as to be positionable in predetermined spaced-apart relation to said lower radius region and oriented to transmit ultrasonic signals into said lower flange, said left loss-of-back transducer being operable in a loss-of-back mode to receive reflections of the ultrasonic signals transmitted thereby; and
said right lower flange shoe further includes:
a right lower web receive transducer mounted so as to be positionable in adjacent, spaced-apart relation to said right lower corner and in alignment with said lower web transmit transducer to receive the ultrasonic signals transmitted thereby; and
a right loss-of-back transducer mounted so as to be positionable in predetermined spaced-apart relation to said lower radius region and oriented to transmit ultrasonic signals into said lower flange, said right loss of back transducer being operable in a loss-of-back mode to receive reflections of the ultrasonic signals transmitted thereby.

34. The probe of claim 33, wherein: said left lower shoe further includes:
a plurality of lower web transmit transducers mounted at spaced-apart positions so that each of said lower web transmit transducers is positionable in predetermined spaced relation to said right lower corner, said lower web transmit transducers being oriented to transmit ultrasonic signals into said web; and
a plurality of loss-of-back transducers mounted at spaced-apart positions so as to be positionable in predetermined spaced-apart relation to said lower radius region and oriented so as to transmit ultrasonic signals into said lower flange, each of said loss-of-back transducers being operable in a loss-of-back mode to receive reflections of the ultrasonic signals transmitted thereby; and
said right lower shoe further includes:
a plurality of lower web receive transducers for receiving the ultrasonic signals transmitted by said plurality of lower web transmit transducers, said lower web receive transducers being mounted at spaced-apart positions that correspond to the spaced-apart positions of said lower web transmit transducers so that each of said lower web receive transducers is alignable with a selected one of said lower web transmit transducers; and a plurality of loss-of-back transducers mounted at spaced-apart positions so as to be positionable in predetermined spaced-apart relation to said lower radius region and oriented so as to transmit ultrasonic signals into said lower flange, each of said loss-of-back transducers being operable in a loss-of-back mode to receive reflections of the ultrasonic signals transmitted thereby.

* * * * *

UNITED STATES PATENT AND TRADEMARK OFFICE
CERTIFICATE OF CORRECTION

PATENT NO. : 4,848,159

DATED : July 18, 1989

INVENTOR(S) : Kennedy et al.

It is certified that error appears in the above-identified patent and that said Letters Patent is hereby corrected as shown below:

| | |
|---|---|
| [57], line 4 (Abstract) | ""T"" should be --"I"-- |
| Column 1, line 49 | "cross-sec-tional" should be --cross-sectional-- |
| Column 2, line 30 | "invention" should be --inventive-- |
| Column 2, line 57 | "flanges" should be --flanged-- |
| Column 3, line 63 | "of" should be --or-- |
| Column 7, line 67 | "principle" should be --principal-- |
| Column 8, line 3 | "s" should be --as-- |
| Column 8, line 32 | "located" should be --locate-- |
| Column 8, line 63 | "of" should be --or-- |
| Column 10, line 15 | "preferable" should be --preferably-- |
| Column 10, line 29 | "preferable" should be --preferably-- |
| Column 10, line 40 | "n" should be --in-- |
| Column 11, line 60 | "preferable" should be --preferably-- |
| Column 15, line 61 | "principle" should be --principal-- |

UNITED STATES PATENT AND TRADEMARK OFFICE
CERTIFICATE OF CORRECTION

PATENT NO. : 4,848,159
DATED : July 18, 1989
INVENTOR(S) : Kennedy et al.

It is certified that error appears in the above-identified patent and that said Letters Patent is hereby corrected as shown below:

| | |
|---|---|
| Column 21, line 41 | "techniques" should be --technique-- |
| Column 22, line 54 | "n" should be --in-- |
| Column 26, line 44 (Claim 9, line 5) | After "forms" insert --said-- |
| Column 34, line 39 (Claim 28, line 39) | "to" should be --top-- |
| Column 1, line 13 | "fibers" should be --fiber-- |

Signed and Sealed this

Eighteenth Day of June, 1991

Attest:

HARRY F. MANBECK, JR.

*Attesting Officer*     *Commissioner of Patents and Trademarks*